United States Patent [19]
Pettit et al.

[11] Patent Number: 5,663,149
[45] Date of Patent: Sep. 2, 1997

[54] HUMAN CANCER INHIBITORY PENTAPEPTIDE HETEROCYCLIC AND HALOPHENYL AMIDES

[75] Inventors: George R. Pettit, Paradise Valley; Jayaram K. Srirangam, Tempe, both of Ariz.; Darko Kantoci, Redlands, Calif.

[73] Assignee: Arizona Board of Regents acting on behalf of Arizona State University, Tempe, Ariz.

[21] Appl. No.: 354,551

[22] Filed: Dec. 13, 1994

[51] Int. Cl.$^6$ .............................. A61K 38/00; C07K 5/00; C07K 7/00
[52] U.S. Cl. .............................. 514/17; 530/330
[58] Field of Search .............................. 530/330, 317; 514/17, 119

[56] References Cited

U.S. PATENT DOCUMENTS 5,410,024   4/1995   Pettit et al. .............................. 530/330
5,502,032   3/1996   Haupt et al. .............................. 514/17

OTHER PUBLICATIONS

Pettit et al., *J. Org. Chem.* v. 59, pp. 2935–2938, 6287–6295, 1994.

Pettit et al., *J. Org. Chem*, v. 59, No. 7, pp. 1796–1800, 1994.

Pettit et al., *Heterocycles*, v. 39, No. 1, pp. 81–100, 1994.

*Primary Examiner*—Avis M. Davenport
*Attorney, Agent, or Firm*—Richard R. Mybeck

[57] ABSTRACT

The synthesis and elucidation of nineteen heterocyclic or halophenyl amide derivatives of dolastatin 10 are disclosed. These compounds and the methods of producing those compounds offer demonstrated significant in vitro activity against several human cancer cell lines. These compounds and the methods of producing those compounds offer a commercially viable alternative to natural and synthetic dolastatin 10.

23 Claims, No Drawings

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,2S*]]]- N,N-dimethyl-L-valyl-N-[2-methoxy-4-[2-[1-methoxy-2- methyl-3-oxo-3-[[3-thiomethyl-1-(2-(4-fluoro- phenylaminocarboxy))propyl]amino]propyl]-1-pyrrolidinyl- 1-(methylpropyl)-4-oxobutyl]-N-methyl-L- valinamide
        ( B ) IDENTIFICATION METHOD: by experiment using high resolution nuclear magnetic resonance and mass spectral techniques
        ( C ) OTHER INFORMATION: This pentapeptide is cell growth inhibitory peptide derivative ( x i ) SEQUENCE DESCRIPTION: SEQ ID NO: 1:

Xaa Val Xaa Xaa Xaa
1                5

( 2 ) INFORMATION FOR SEQ ID NO: 2:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
    ( A ) NAME/KEY: [2S-[1[1R*(R*),2S*],2R*[1S*,
        2S*]]]- N,N-dimethyl-L-valyl-N-[2-methoxy-4-[2-[1-
        methoxy-2- methyl-3-oxo-3-[[3-thiomethyl-1-(2-(2-
        chloro- phenylaminocarboxy))propyl]amino]propyl]-1-
        pyrrolidinyl- 1-(methylpropyl)-4-oxobutyl]-N-
        methyl-L- valinamide
    ( B ) IDENTIFICATION METHOD: by experiment
        using high resolution nuclear magnetic
        resonance and mass spectral techniques
    ( C ) OTHER INFORMATION: This pentapeptide is
        cell growth inhibitory peptide derivative ( x i ) SEQUENCE DESCRIPTION: SEQ ID NO: 2:

Xaa  Val  Xaa  Xaa  Xaa
 1                 5

( 2 ) INFORMATION FOR SEQ ID NO: 3:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,
            2S*]]]- N,N-dimethyl-L-valyl-N-[2-methoxy-4-[2-[1-
            methoxy-2- methyl-3-oxo-3-[[3-thiomethyl-1-(2-(3-
            chloro- phenylaminocarboxy))propyl]amino]propyl]-1-
            pyrrolidinyl- 1-(methylpropyl)-4-oxobutyl]-N-
            methyl-L- valinamide
        ( B ) IDENTIFICATION METHOD: by experiment
            using high resolution nuclear magnetic resonance
            and mass spectral techniques
        ( C ) OTHER INFORMATION: This pentapeptide
            is cell growth inhibitory peptide derivative ( x i ) SEQUENCE DESCRIPTION: SEQ ID NO: 3:

Xaa  Val  Xaa  Xaa  Xaa
 1                 5

( 2 ) INFORMATION FOR SEQ ID NO: 4:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,
            2S*]]]- N,N-dimethyl-L-valyl-N-[2-methoxy-4-[2-[1-
            methoxy-2- methyl-3-oxo-3-[[2-phenyl-1-(2-(3-
            chloro- phenylaminocarboxy))ethyl]amino]propyl]-1-
            pyrrolidinyl- 1-(methylpropyl)-4-oxobutyl]-N-
            methyl-L- valinamide
        ( B ) IDENTIFICATION METHOD: by experiment
            using high resolution nuclear magnetic resonance
            and mass spectral techniques
        ( C ) OTHER INFORMATION: This pentapeptide
            is cell growth inhibitory peptide derivative ( x i ) SEQUENCE DESCRIPTION: SEQ ID NO: 4:

Xaa Val Xaa Xaa Xaa
1              5

( 2 ) INFORMATION FOR SEQ ID NO: 5:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,
        2S*]]]- N,N-dimethyl-L-valyl-N-[2-methoxy-4-[2-[1-
        methoxy-2- methyl-3-oxo-3-[[3-thiomethyl-1-(2-
        ( 4 - c h l o r o -  p h e n y l a m i n o c a r b o x y ))propyl]amino]propyl]-
        1- pyrrolidinyl-1-(methylpropyl)-4-oxobutyl]-N-
        methyl-L- valinamide
        ( B ) IDENTIFICATION METHOD: by experiment
        using high resolution nuclear magnetic resonance
        and mass spectral techniques
        ( C ) OTHER INFORMATION: This pentapeptide
        is cell growth inhibitory peptide derivative ( x i ) SEQUENCE DESCRIPTION: SEQ ID NO: 5:

Xaa Val Xaa Xaa Xaa
1              5

( 2 ) INFORMATION FOR SEQ ID NO: 6:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,
        2S*]]]- N,N-dimethyl-L-valyl-N-[2-methoxy-4-[2-[1-
        methoxy-2- methyl-3-oxo-3-[[2-phenyl-1-(2-(4-
        chloro- phenylaminocarboxy))ethyl]amino]propyl]-
        1- pyrrolidinyl-1-(methylpropyl)-4-oxobutyl]-N-
        methyl-L- valinamide
        ( B ) IDENTIFICATION METHOD: by experiment
        using high resolution nuclear magnetic resonance
        and mass spectral techniques
        ( C ) OTHER INFORMATION: This pentapeptide
        is cell growth inhibitory peptide derivative ( x i ) SEQUENCE DESCRIPTION: SEQ ID NO: 6:

Xaa Val Xaa Xaa Xaa
1              5

( 2 ) INFORMATION FOR SEQ ID NO: 7:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:

(A) DESCRIPTION: Linear pentapeptide (iii) HYPOTHETICAL: no (iv) ANTI-SENSE: no (ix) FEATURE:
(A) NAME/KEY: [2S-[1[1R*(R*),2S*],2R*[1S*,
2S*]]]- N,N-dimethyl-L-valyl-N-[2-methoxy-4-[2-[1-
methoxy-2- methyl-3-oxo-3-[[3-thiomethyl-1-(2-
(2,5-dichloro-phenylaminocarboxy))propyl]
amino]propyl]-1-pyrrolidinyl-1-(methylpropyl)-
4-oxobutyl]-N-methyl-L-valinamide
(B) IDENTIFICATION METHOD: by experiment
using high resolution nuclear magnetic resonance
and mass spectral techniques
(C) OTHER INFORMATION: This pentapeptide
is cell growth inhibitory peptide derivative (xi) SEQUENCE DESCRIPTION: SEQ ID NO: 7:

Xaa  Val  Xaa  Xaa  Xaa
 1              5

(2) INFORMATION FOR SEQ ID NO: 8:

(i) SEQUENCE CHARACTERISTICS:
(A) LENGTH: 5 amino acid residues
(B) TYPE: amino acid
(D) TOPOLOGY: linear (ii) MOLECULE TYPE:
(A) DESCRIPTION: Linear pentapeptide (iii) HYPOTHETICAL: no (iv) ANTI-SENSE: no (ix) FEATURE:
(A) NAME/KEY: [2S-[1[1R*(R*),2S*],2R*[1S*,
2S*]]]- N,N-dimethyl-L-valyl-N-[2-methoxy-4-[2-[1-
methoxy-2- methyl-3-oxo-3-[[2-phenyl-1-(2-(2,5-
dichloro- phenylaminocarboxy))ethyl]amino]propyl]
- 1- pyrrolidinyl-1-(methylpropyl)-4-oxobutyl]-N-
methyl-L- valinamide
(B) IDENTIFICATION METHOD: by experiment
using high resolution nuclear magnetic resonance
and mass spectral techniques
(C) OTHER INFORMATION: This pentapeptide
is cell growth inhibitory peptide derivative (xi) SEQUENCE DESCRIPTION: SEQ ID NO: 8:

Xaa  Val  Xaa  Xaa  Xaa
 1              5

(2) INFORMATION FOR SEQ ID NO: 9:

(i) SEQUENCE CHARACTERISTICS:
(A) LENGTH: 5 amino acid residues
(B) TYPE: amino acid
(D) TOPOLOGY: linear (ii) MOLECULE TYPE:
(A) DESCRIPTION: Linear pentapeptide (iii) HYPOTHETICAL: no (iv) ANTI-SENSE: no (ix) FEATURE:
(A) NAME/KEY: [2S-[1[1R*(R*),2S*],2R*[1S*,
2S*]]]- N,N-dimethyl-L-valyl-N-[2-methoxy-4-[2-[1-
methoxy-2- methyl-3-oxo-3-[[3-thiomethyl-1-(2-(2-
(4-chlorophenyl)ethylaminocarboxy))propyl]amino]
propyl]-1- pyrrolidinyl-1-(methylpropyl)-4-
oxobutyl]- N-methyl-L-valinamide ( B ) IDENTIFICATION METHOD: by experiment
using high resolution nuclear magnetic resonance
and mass spectral techniques
( C ) OTHER INFORMATION: This pentapeptide
is cell growth inhibitory peptide derivative ( x i ) SEQUENCE DESCRIPTION: SEQ ID NO: 9:

Xaa Val Xaa Xaa Xaa
1           5

( 2 ) INFORMATION FOR SEQ ID NO: 10:

( i ) SEQUENCE CHARACTERISTICS:
( A ) LENGTH: 5 amino acid residues
( B ) TYPE: amino acid
( D ) TOPOLOGY: linear ( i i ) MOLECULE TYPE:
( A ) DESCRIPTION: Linear pentapeptide ( i i i ) HYPOTHETICAL: no ( i v ) ANTI-SENSE: no ( i x ) FEATURE:
( A ) NAME/KEY: [2S-[1[1R*(R*),2S*],2R*[1S*,
2S*]]]- N,N-dimethyl-L-valyl-N-[2-methoxy-4-[2-
[ 1- methoxy-2-methyl-3-oxo-3-[[2-phenyl-1-(2-
( 6 - f l u o r o -  b e n z o t h i a z o l - 2 - a m i n o c a r b o x y ))ethyl]
amino]propyl]-1-pyrrolidinyl-1-(methylpropyl)-
4-oxobutyl]-N-methyl-L-valinamide
( B ) IDENTIFICATION METHOD: by experiment
using high resolution nuclear magnetic resonance
and mass spectral techniques
( C ) OTHER INFORMATION: This pentapeptide
is cell growth inhibitory peptide derivative ( x i ) SEQUENCE DESCRIPTION: SEQ ID NO: 10:

Xaa Val Xaa Xaa Xaa
1           5

( 2 ) INFORMATION FOR SEQ ID NO: 11:

( i ) SEQUENCE CHARACTERISTICS:
( A ) LENGTH: 5 amino acid residues
( B ) TYPE: amino acid
( D ) TOPOLOGY: linear ( i i ) MOLECULE TYPE:
( A ) DESCRIPTION: Linear pentapeptide ( i i i ) HYPOTHETICAL: no ( i v ) ANTI-SENSE: no ( i x ) FEATURE:
( A ) NAME/KEY: [2S-[1[1R*(R*),2S*],2R*[1S*,
2S*]]]- N,N-dimethyl-L-valyl-N-[2-methoxy-4-[2-
[ 1- methoxy-2-methyl-3-oxo-3-[[2-phenyl-1-(2-
( 6 - c h l o r o -  b e n z o t h i a z o l - 2 - a m i n o c a r b o x y ))ethyl]
amino]propyl]-1-pyrrolidinyl-1-(methylpropyl)-
4-oxobutyl]-N-methyl-L-valinamide
( B ) IDENTIFICATION METHOD: by experiment
using high resolution nuclear magnetic resonance
and mass spectral techniques
( C ) OTHER INFORMATION: This pentapeptide
is cell growth inhibitory peptide derivative ( x i ) SEQUENCE DESCRIPTION: SEQ ID NO: 11:

Xaa Val Xaa Xaa Xaa
1           5

( 2 ) INFORMATION FOR SEQ ID NO: 12:

( i ) SEQUENCE CHARACTERISTICS:
   ( A ) LENGTH: 5 amino acid residues
   ( B ) TYPE: amino acid
   ( D ) TOPOLOGY: linear ( i i ) MOLECULE TYPE:
   ( A ) DESCRIPTION: Linear pentapeptide ( i i i ) HYPOTHETICAL: no ( i v ) ANTI-SENSE: no ( i x ) FEATURE:
   ( A ) NAME/KEY: [2S-[1[1R*(R*),2S*],2R*[1S*,
       2S*]]]- N,N-dimethyl-L-valyl-N-[2-methoxy-4-[2-
       [ 1- methoxy-2-methyl-3-oxo-3-[[2-(4-chloro-
       phenyl)-1-(2- (6-chloro-benzothiazol-2-amino
       carboxy))ethyl]amino]propyl]-1-pyrrolidinyl-1-
       (methylpropyl)-4-oxobutyl]-N-methyl-L- valinamide
   ( B ) IDENTIFICATION METHOD: by experiment
       using high resolution nuclear magnetic resonance
       and mass spectral techniques
   ( C ) OTHER INFORMATION: This pentapeptide
       is cell growth inhibitory peptide derivative ( x i ) SEQUENCE DESCRIPTION: SEQ ID NO: 12:

Xaa  Val  Xaa  Xaa  Xaa
1              5

( 2 ) INFORMATION FOR SEQ ID NO: 13:

( i ) SEQUENCE CHARACTERISTICS:
   ( A ) LENGTH: 5 amino acid residues
   ( B ) TYPE: amino acid
   ( D ) TOPOLOGY: linear ( i i ) MOLECULE TYPE:
   ( A ) DESCRIPTION: Linear pentapeptide ( i i i ) HYPOTHETICAL: no ( i v ) ANTI-SENSE: no ( i x ) FEATURE:
   ( A ) NAME/KEY: [2S-[1[1R*(R*),2S*],2R*[1S*,
       2S*]]]- N,N-dimethyl-L-valyl-N-[2-methoxy-4-[2-
       [ 1- methoxy-2-methyl-3-oxo-3-[[3-thiomethyl-
       1-(2- (benzothiazol-2-aminocarboxy)propyl]
       amino]propyl]-1-pyrrolidinyl-1-(methylpropyl)-
       4-oxobutyl]-N-methyl-L-valinamide
   ( B ) IDENTIFICATION METHOD: by experiment
       using high resolution nuclear magnetic resonance
       and mass spectral techniques
   ( C ) OTHER INFORMATION: This pentapeptide
       is cell growth inhibitory peptide derivative ( x i ) SEQUENCE DESCRIPTION: SEQ ID NO: 13:

Xaa  Val  Xaa  Xaa  Xaa
1              5

( 2 ) INFORMATION FOR SEQ ID NO: 14:

( i ) SEQUENCE CHARACTERISTICS:
   ( A ) LENGTH: 5 amino acid residues
   ( B ) TYPE: amino acid
   ( D ) TOPOLOGY: linear ( i i ) MOLECULE TYPE:
   ( A ) DESCRIPTION: Linear pentapeptide ( i i i ) HYPOTHETICAL: no ( i v ) ANTI-SENSE: no ( i x ) FEATURE:
   ( A ) NAME/KEY: [2S-[1[1R*(R*),2S*],2R*[1S*, 2S*]]]- N,N-dimethyl-L-valyl-N-[2-methoxy-4-[2-
[ 1- methoxy-2-methyl-3-oxo-3-[[(1-benzothiazol-
2- aminocarboxy)pyrrolidinyl]prolyl]propyl]-1-
pyrrolidinyl- 1-(methylpropyl)-4-oxobutyl]-N-
methyl-L- valinamide
( B ) IDENTIFICATION METHOD: by experiment
using high resolution nuclear magnetic resonance
and mass spectral techniques
( C ) OTHER INFORMATION: This pentapeptide
is cell growth inhibitory peptide derivative ( x i ) SEQUENCE DESCRIPTION: SEQ ID NO: 14:

Xaa Val Xaa Xaa Xaa
1           5

( 2 ) INFORMATION FOR SEQ ID NO: 15:

( i ) SEQUENCE CHARACTERISTICS:
( A ) LENGTH: 5 amino acid residues
( B ) TYPE: amino acid
( D ) TOPOLOGY: linear ( i i ) MOLECULE TYPE:
( A ) DESCRIPTION: Linear pentapeptide ( i i i ) HYPOTHETICAL: no ( i v ) ANTI-SENSE: no ( i x ) FEATURE:
( A ) NAME/KEY: [2S-[1[1R*(R*),2S*],2R*[1S*,
2S*]]]- N,N-dimethyl-L-valyl-N-[2-methoxy-4-[2-
[ 1- methoxy-2-methyl-3-oxo-3-[[3-thiomethyl-1-

( 2 - ( pyridin-2- aminocarboxy)propyl]amino]
propyl]-1- pyrrolidinyl-1-(methylpropyl)-4-
oxobutyl]- N-methyl-L-valinamide
( B ) IDENTIFICATION METHOD: by experiment
using high resolution nuclear magnetic resonance
and mass spectral techniques
( C ) OTHER INFORMATION: This pentapeptide
is cell growth inhibitory peptide derivative ( x i ) SEQUENCE DESCRIPTION: SEQ ID NO: 15:

Xaa Val Xaa Xaa Xaa
1           5

( 2 ) INFORMATION FOR SEQ ID NO: 16:

( i ) SEQUENCE CHARACTERISTICS:
( A ) LENGTH: 5 amino acid residues
( B ) TYPE: amino acid
( D ) TOPOLOGY: linear ( i i ) MOLECULE TYPE:
( A ) DESCRIPTION: Linear pentapeptide ( i i i ) HYPOTHETICAL: no ( i v ) ANTI-SENSE: no ( i x ) FEATURE:
( A ) NAME/KEY: [2S-[1[1R*(R*),2S*],2R*[1S*,
2S*]]]- N,N-dimethyl-L-valyl-N-[2-methoxy-4-
[ 2- [1-methoxy-2-methyl-3-oxo-3-[[3-thiomethyl-
1-(2- (quinolin-3-aminocarboxy)propyl]amino]
propyl]-1- pyrrolidinyl-1-(methylpropyl)-4-
oxobutyl]- N-methyl-L-valinamide
( B ) IDENTIFICATION METHOD: by experiment
using high resolution nuclear magnetic resonance
and mass spectral techniques
( C ) OTHER INFORMATION: This pentapeptide
is cell growth inhibitory peptide derivative ( x i ) SEQUENCE DESCRIPTION: SEQ ID NO: 16:

Xaa Val Xaa Xaa Xaa
1             5

( 2 ) INFORMATION FOR SEQ ID NO: 17:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,
              2S*]]]- N,N-dimethyl-L-valyl-N-[2-methoxy-4-
              [ 2- [1-methoxy-2-methyl-3-oxo-3-[[(1-(quinolin-
              3- aminocarboxy)pyrrolidinyl]propyl]-1-
              pyrrolidinyl- 1-(methylpropyl)-4-oxobutyl]-N-
              methyl-L- valinamide
        ( B ) IDENTIFICATION METHOD: by experiment
              using high resolution nuclear magnetic resonance
              and mass spectral techniques
        ( C ) OTHER INFORMATION: This pentapeptide
              is cell growth inhibitory peptide derivative ( x i ) SEQUENCE DESCRIPTION: SEQ ID NO: 17:

Xaa Val Xaa Xaa Xaa
1             5

( 2 ) INFORMATION FOR SEQ ID NO: 18:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( i x ) FEATURE:
        ( A ) NAME/KEY: [2S-[1[1R*(R*),2S*],2R*[1S*,
              2S*]]]- N,N-dimethyl-L-valyl-N-[2-methoxy-4-
              [ 2- [1-methoxy-2-methyl-3-oxo-3-[[2-methyl-1-
(2-quinolin-3-aminocarboxy)propyl]amino]
              propyl]-1- pyrrolidinyl-1-(methylpropyl)-4-
              oxobutyl]- N-methyl-L-valinamide
        ( B ) IDENTIFICATION METHOD: by experiment
              using high resolution nuclear magnetic resonance
              and mass spectral techniques
        ( C ) OTHER INFORMATION: This pentapeptide
              is cell growth inhibitory peptide derivative ( x i ) SEQUENCE DESCRIPTION: SEQ ID NO: 18:

Xaa Val Xaa Xaa Xaa
1             5

( 2 ) INFORMATION FOR SEQ ID NO: 19:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide (iii) HYPOTHETICAL: no (iv) ANTI-SENSE: no (ix) FEATURE:
   (A) NAME/KEY: [2S-[1[1R*(R*),2S*],2R*[1S*,
       2S*]]]- N,N-dimethyl-L-valyl-N-[2-methoxy-4-[2-
       [1- methoxy-2-methyl-3-oxo-3-[[2S-methyl-1-(2-
       quinolin-3- aminocarboxy)butyl]amino]propyl]-
       1- pyrrolidinyl-1-(methylpropyl)-4-oxobutyl]-
       N-methyl-L- valinamide
   (B) IDENTIFICATION METHOD: by experiment
       using high resolution nuclear magnetic resonance
       and mass spectral techniques
   (C) OTHER INFORMATION: This pentapeptide
       is cell growth inhibitory peptide derivative (xi) SEQUENCE DESCRIPTION: SEQ ID NO: 19:

Xaa Val Xaa Xaa Xaa
1           5

HUMAN CANCER INHIBITORY PENTAPEPTIDE HETEROCYCLIC AND HALOPHENYL AMIDES

This research was funded in part by Outstanding Investigator Grant CA 44344-01-04-05 awarded by the National Cancer Institute, DHHS. The United States Government may have certain rights to this invention.

INTRODUCTION

This invention relates generally to the field of chemotherapeutic agents and more particularly to pentapeptide heterocyclic and halophenyl amide derivatives of dolastatin 10.

BACKGROUND OF THE INVENTION

Ancient marine invertebrate species of the Phyla Bryozoa, Molluska, and Porifera have been well established in the oceans for over one billion years. Such organisms have undergone trillions of biosynthetic reactions in their evolutionary chemistry to reach their present level of cellular organization, regulation and defense.

Marine sponges, however, have changed minimally in their physical appearance over the last 500 million years. This suggests a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. sea hare extracts were being used in Greece for their curative affect. This consideration along with the observation that marine animals, e.g., invertebrates and sharks, rarely develop cancer led to the systematic investigation of marine animal and plant anticancer compounds.

By 1968 ample evidence had been obtained, based on the U.S. National Cancer Institute's (NCI) key experimental cancer study systems, that certain marine organisms could provide new and anti-neoplastic and/or cytotoxic agents and might also lead to compounds which would be effective in the control and/or eradication of vital diseases. Further, these marine organisms were believed to possess potentially useful drug candidates of unprecedented structure which had eluded discovery by other methods of medicinal chemistry. Fortunately, these expectations have been realized, e.g., the discovery of the bryostatins, dolastatins and cephalostatins, many of which are now in preclinical or human clinical studies.

Those researchers presently involved in medicinal chemistry know well the time lag between the isolation of a new compound and its introduction to the market. This procedure takes several years and often takes decades. Accordingly, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop this necessary data approaches ten million dollars per compound. Such a large investment will be made only when there is a reasonable opportunity for it to be recovered. Absent such opportunity, there will be no investment and the research involving the discovery of these potentially life saving compounds will cease.

Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and has been accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, October 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports*, Vol. 81, No. 14, Page 1088, Jul. 14, 1989, for a description of the methods of statistical analysis. Each of these references are incorporated herein by this reference thereto.

Numerous substances have been discovered which demonstrate significant anti-neoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing anti-neoplastic qualities. The collection and processing of these latter compounds from their natural sources ranges from grossly impractical to the utterly impossible. Ignoring the ecological impact of such harvesting, the population of these creatures and the cost of collection and extraction make the process unworkable. Artificial synthesis of the active compounds is the only possible solution.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The impairment of human cancerous tumor growth is utilitarian in that it relieves these conditions, thereby allowing the human thus affected to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive for further research.

The recognition of anti-neoplastic and tumor inhibiting activity as demonstrated by accepted NCI criteria as "utility" can promote research efforts in the United States and is unequivocally essential if those efforts are to obtain even a modest modicum of success.

BRIEF SUMMARY OF THE INVENTION

The synthesis of potentially useful peptides presents one of the most essential and promising approaches to new types of anticancer and immunosuppressant drugs. Presented herein are the synthesis of several pentapeptides involving modified amino acids and carrying heterocyclic or halophenyl groups at the C-terminus. The modified amino acids chosen here are the constituents of the well known marine peptide Dolastatin 10, which exhibits one of the best anti-neoplastic activity profiles against various cancer screens known to date. Unique structural modifications have been carried out in order to achieve the synthesis of new pentapeptides carrying heterocyclic/halophenyl groups at the C-terminus and possessing extraordinary anti-neoplastic and/or cytostatic activity.

This research has led to an effective method for the synthesis of new and very potent anti-cancer pentapeptides. The present invention involves the synthesis of nineteen such pentapeptides as shown below. Accordingly, the primary object of the subject invention is the synthesis of nineteen pentapeptide amides which exhibit effective anti-neoplastic activity against various human cancer and mouse leukemia (P-388) tumor cell lines.

The general process and abbreviations set forth in this disclosure is as set forth below:

Abbreviations

4FPh = 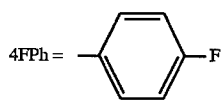

2ClPh = 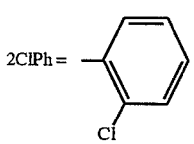

3ClPh = 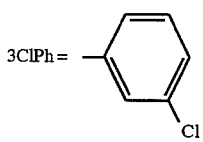

4ClPh = 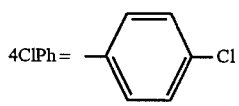

2,5diClPh = 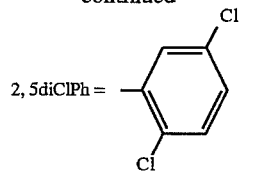

4ClPEA = 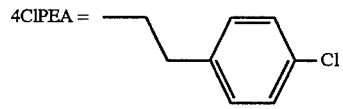

6FBnThz = 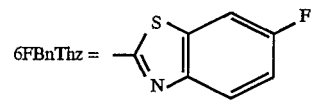

6ClBnThz = 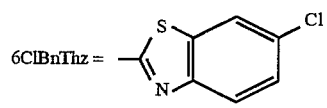

BnThz = 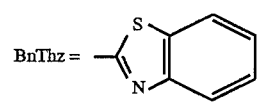

2Py = 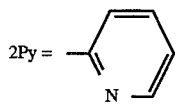

3Q = 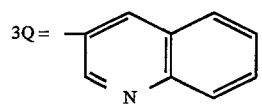

pCl-Phe = 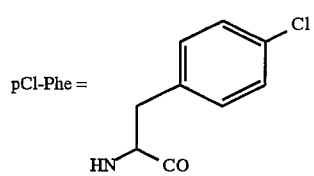

FIG. 1

$$\text{Boc—X—OH} + \text{Ar—NH}_2 \xrightarrow{\text{Coupling reag.}} \text{Boc—X—N}^{Ar}_{H}$$

| 1 | 2 | 3 |
|---|---|---|
| a) X = Met | a) Ar = 4FPh | a) X = Met, Ar = 4FPh |
| b) X = Phe | b) Ar = 2ClPh | b) X = Met, Ar = 2ClPh |
| c) X = Pro | c) Ar = 3ClPh | c) X = Met, Ar = 3ClPh |
| d) X = Val | d) Ar = 4ClPh | d) X = Phe, Ar = 3ClPh |
| e) X = Ile | e) Ar = 2,5diClPh | e) X = Met, Ar = 4ClPh |
| f) X = pCl—Phe | f) Ar = 4ClPEA | f) X = Phe, Ar = 4ClPh |
| | g) Ar = 6FBnThz | g) X = Met, Ar = 2,5diClPh |
| | h) Ar = 6ClBnThz | h) X = Phe, Ar = 2,5diClPh |
| | i) Ar = BnThz | i) X = Met, Ar = 4ClPEA |
| | j) Ar = 2Py | j) X = Phe, Ar = 6FBnThz |
| | k) Ar = 3Q | k) X = Phe, Ar = 6ClBnThz |
| | | l) X = pCl—Phe, Ar = 6ClBnThz |
| | | m) X = Met, Ar = BnThz |
| | | n) X = Pro, Ar = BnThz |
| | | o) X = Met, Ar = 2Py |
| | | p) X = Met, Ar = 3Q |
| | | q) X = Pro, Ar = 3Q |
| | | r) X = Val, Ar = 3Q |
| | | s) X = Ile, Ar = 3Q |

FIG. 2

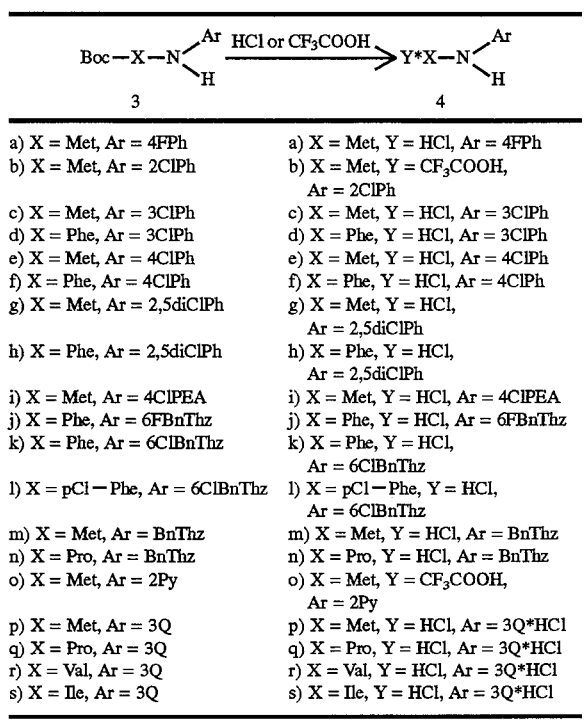

| | |
|---|---|
| a) X = Met, Ar = 4FPh | a) X = Met, Y = HCl, Ar = 4FPh |
| b) X = Met, Ar = 2ClPh | b) X = Met, Y = CF₃COOH, Ar = 2ClPh |
| c) X = Met, Ar = 3ClPh | c) X = Met, Y = HCl, Ar = 3ClPh |
| d) X = Phe, Ar = 3ClPh | d) X = Phe, Y = HCl, Ar = 3ClPh |
| e) X = Met, Ar = 4ClPh | e) X = Met, Y = HCl, Ar = 4ClPh |
| f) X = Phe, Ar = 4ClPh | f) X = Phe, Y = HCl, Ar = 4ClPh |
| g) X = Met, Ar = 2,5diClPh | g) X = Met, Y = HCl, Ar = 2,5diClPh |
| h) X = Phe, Ar = 2,5diClPh | h) X = Phe, Y = HCl, Ar = 2,5diClPh |
| i) X = Met, Ar = 4ClPEA | i) X = Met, Y = HCl, Ar = 4ClPEA |
| j) X = Phe, Ar = 6FBnThz | j) X = Phe, Y = HCl, Ar = 6FBnThz |
| k) X = Phe, Ar = 6ClBnThz | k) X = Phe, Y = HCl, Ar = 6ClBnThz |
| l) X = pCl—Phe, Ar = 6ClBnThz | l) X = pCl—Phe, Y = HCl, Ar = 6ClBnThz |
| m) X = Met, Ar = BnThz | m) X = Met, Y = HCl, Ar = BnThz |
| n) X = Pro, Ar = BnThz | n) X = Pro, Y = HCl, Ar = BnThz |
| o) X = Met, Ar = 2Py | o) X = Met, Y = CF₃COOH, Ar = 2Py |
| p) X = Met, Ar = 3Q | p) X = Met, Y = HCl, Ar = 3Q*HCl |
| q) X = Pro, Ar = 3Q | q) X = Pro, Y = HCl, Ar = 3Q*HCl |
| r) X = Val, Ar = 3Q | r) X = Val, Y = HCl, Ar = 3Q*HCl |
| s) X = Ile, Ar = 3Q | s) X = Ile, Y = HCl, Ar = 3Q*HCl |

FIG. 3

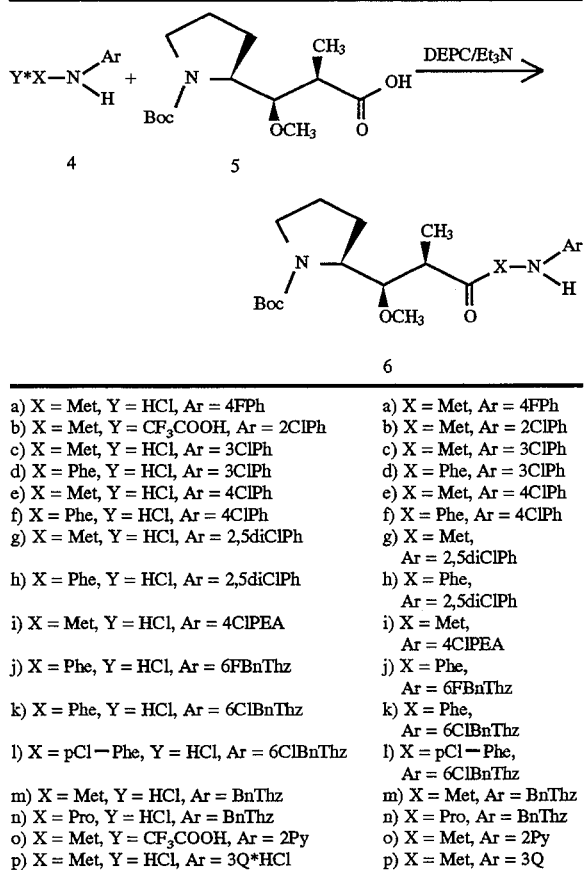

| | |
|---|---|
| a) X = Met, Y = HCl, Ar = 4FPh | a) X = Met, Ar = 4FPh |
| b) X = Met, Y = CF₃COOH, Ar = 2ClPh | b) X = Met, Ar = 2ClPh |
| c) X = Met, Y = HCl, Ar = 3ClPh | c) X = Met, Ar = 3ClPh |
| d) X = Phe, Y = HCl, Ar = 3ClPh | d) X = Phe, Ar = 3ClPh |
| e) X = Met, Y = HCl, Ar = 4ClPh | e) X = Met, Ar = 4ClPh |
| f) X = Phe, Y = HCl, Ar = 4ClPh | f) X = Phe, Ar = 4ClPh |
| g) X = Met, Y = HCl, Ar = 2,5diClPh | g) X = Met, Ar = 2,5diClPh |
| h) X = Phe, Y = HCl, Ar = 2,5diClPh | h) X = Phe, Ar = 2,5diClPh |
| i) X = Met, Y = HCl, Ar = 4ClPEA | i) X = Met, Ar = 4ClPEA |
| j) X = Phe, Y = HCl, Ar = 6FBnThz | j) X = Phe, Ar = 6FBnThz |
| k) X = Phe, Y = HCl, Ar = 6ClBnThz | k) X = Phe, Ar = 6ClBnThz |
| l) X = pCl—Phe, Y = HCl, Ar = 6ClBnThz | l) X = pCl—Phe, Ar = 6ClBnThz |
| m) X = Met, Y = HCl, Ar = BnThz | m) X = Met, Ar = BnThz |
| n) X = Pro, Y = HCl, Ar = BnThz | n) X = Pro, Ar = BnThz |
| o) X = Met, Y = CF₃COOH, Ar = 2Py | o) X = Met, Ar = 2Py |
| p) X = Met, Y = HCl, Ar = 3Q*HCl | p) X = Met, Ar = 3Q |
| q) X = Pro, Y = HCl, Ar = 3Q*HCl | q) X = Pro, Ar = 3Q |
| r) X = Val, Y = HCl, Ar = 3Q*HCl | r) X = Val, Ar = 3Q |
| s) X = Ile, Y = HCl, Ar = 3Q*HCl | s) X = Ile, Ar = 3Q |

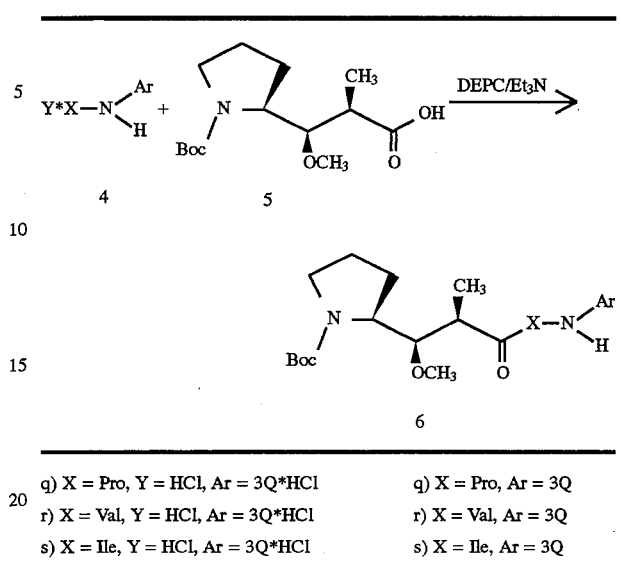

FIG. 4

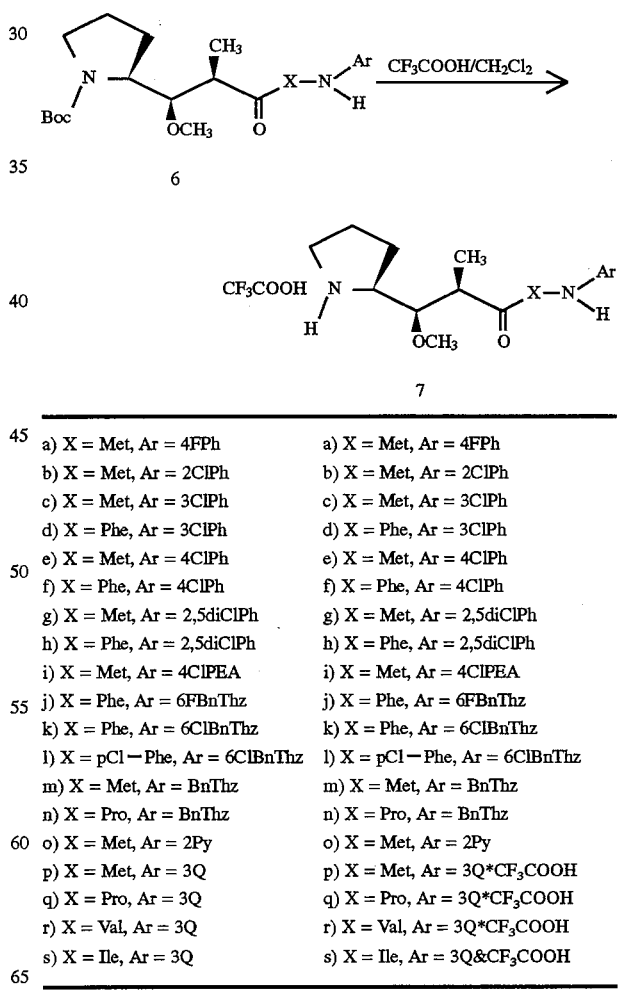

| | |
|---|---|
| a) X = Met, Ar = 4FPh | a) X = Met, Ar = 4FPh |
| b) X = Met, Ar = 2ClPh | b) X = Met, Ar = 2ClPh |
| c) X = Met, Ar = 3ClPh | c) X = Met, Ar = 3ClPh |
| d) X = Phe, Ar = 3ClPh | d) X = Phe, Ar = 3ClPh |
| e) X = Met, Ar = 4ClPh | e) X = Met, Ar = 4ClPh |
| f) X = Phe, Ar = 4ClPh | f) X = Phe, Ar = 4ClPh |
| g) X = Met, Ar = 2,5diClPh | g) X = Met, Ar = 2,5diClPh |
| h) X = Phe, Ar = 2,5diClPh | h) X = Phe, Ar = 2,5diClPh |
| i) X = Met, Ar = 4ClPEA | i) X = Met, Ar = 4ClPEA |
| j) X = Phe, Ar = 6FBnThz | j) X = Phe, Ar = 6FBnThz |
| k) X = Phe, Ar = 6ClBnThz | k) X = Phe, Ar = 6ClBnThz |
| l) X = pCl—Phe, Ar = 6ClBnThz | l) X = pCl—Phe, Ar = 6ClBnThz |
| m) X = Met, Ar = BnThz | m) X = Met, Ar = BnThz |
| n) X = Pro, Ar = BnThz | n) X = Pro, Ar = BnThz |
| o) X = Met, Ar = 2Py | o) X = Met, Ar = 2Py |
| p) X = Met, Ar = 3Q | p) X = Met, Ar = 3Q*CF₃COOH |
| q) X = Pro, Ar = 3Q | q) X = Pro, Ar = 3Q*CF₃COOH |
| r) X = Val, Ar = 3Q | r) X = Val, Ar = 3Q*CF₃COOH |
| s) X = Ile, Ar = 3Q | s) X = Ile, Ar = 3Q&CF₃COOH |

FIG. 5

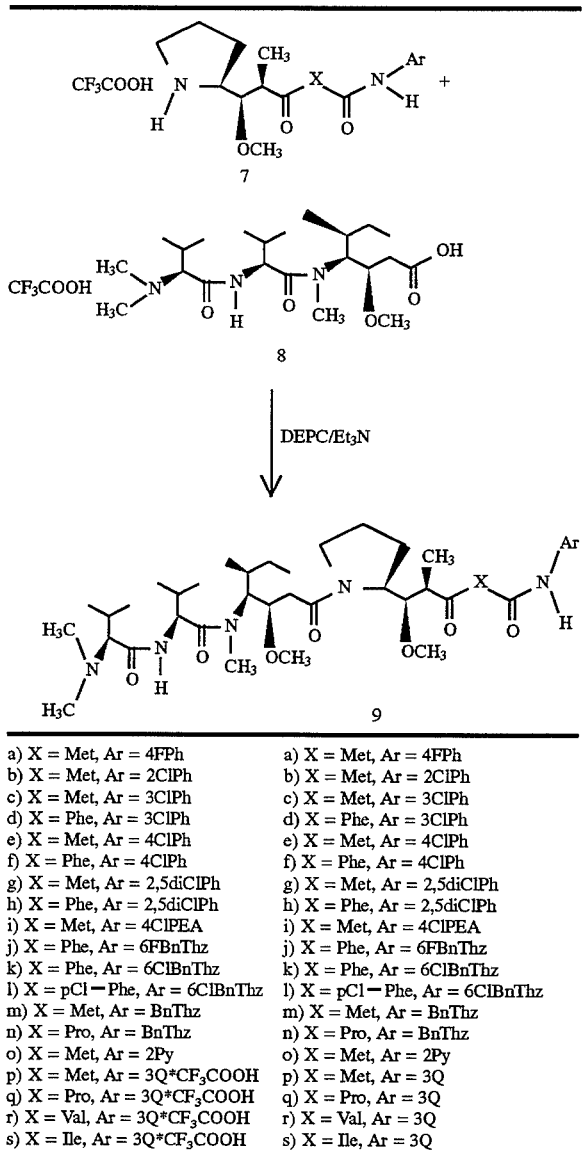

| | |
|---|---|
| a) X = Met, Ar = 4FPh | a) X = Met, Ar = 4FPh |
| b) X = Met, Ar = 2ClPh | b) X = Met, Ar = 2ClPh |
| c) X = Met, Ar = 3ClPh | c) X = Met, Ar = 3ClPh |
| d) X = Phe, Ar = 3ClPh | d) X = Phe, Ar = 3ClPh |
| e) X = Met, Ar = 4ClPh | e) X = Met, Ar = 4ClPh |
| f) X = Phe, Ar = 4ClPh | f) X = Phe, Ar = 4ClPh |
| g) X = Met, Ar = 2,5diClPh | g) X = Met, Ar = 2,5diClPh |
| h) X = Phe, Ar = 2,5diClPh | h) X = Phe, Ar = 2,5diClPh |
| i) X = Met, Ar = 4ClPEA | i) X = Met, Ar = 4ClPEA |
| j) X = Phe, Ar = 6FBnThz | j) X = Phe, Ar = 6FBnThz |
| k) X = Phe, Ar = 6ClBnThz | k) X = Phe, Ar = 6ClBnThz |
| l) X = pCl—Phe, Ar = 6ClBnThz | l) X = pCl—Phe, Ar = 6ClBnThz |
| m) X = Met, Ar = BnThz | m) X = Met, Ar = BnThz |
| n) X = Pro, Ar = BnThz | n) X = Pro, Ar = BnThz |
| o) X = Met, Ar = 2Py | o) X = Met, Ar = 2Py |
| p) X = Met, Ar = 3Q*CF$_3$COOH | p) X = Met, Ar = 3Q |
| q) X = Pro, Ar = 3Q*CF$_3$COOH | q) X = Pro, Ar = 3Q |
| r) X = Val, Ar = 3Q*CF$_3$COOH | r) X = Val, Ar = 3Q |
| s) X = Ile, Ar = 3Q*CF$_3$COOH | s) X = Ile, Ar = 3Q |

The modification mentioned here introduces a peptide bond between different amino acids (1a–f) and various aromatic amine moieties (2a–k) obtaining pentapeptide amides (9a–s) respectively. See FIG. 1, supra.

As a first step the corresponding amines (2a–k) were allowed to react with Boc-L-aminoacids (1a–f). The amines were: 4-fluoroaniline (2a); 2-chloroaniline (2b); 3-chloroaniline (2c); 4-chloroaniline (2d); 2,5-dichloroaniline (2e); 4-chlorophenethylamine (2f); 2-amino-6-fluorobenzothiazole (2g); 2-amino-6-chlorobenzothiazole (2h); 2-aminobenzothiazole (2i); 2-aminopyridine (2j); 3-aminoquinoline (2k); and the aminoacids were: N-tert-Boc-Methionine (1a); N-tert-Boc-Phenylalanine (1b); N-tert-Boc-Proline (1c); N-tert-Boc-Valine (1d); N-tert-Boc-Isoleucine (1e); Synthesis of amides (3a–s) in the presence of 2-ethoxy-1-ethoxycarbonyl-1,2-dihydroquinoline (EEDQ) or isobutylchloroformate or 1,3-dicyclohexylcarbodiimide as condensing agents led to excellent yields. No racemization was observed during these reactions.

As shown in FIG. 2, supra, the protecting group (N-tert-Boc) of the above amides (3a–s) was removed with hydrogen chloride in acetic acid or hydrogen chloride in dioxane or trifluoroacetic acid in methylene chloride to afford the corresponding hydrochloride or trifluoroacetate salts (4a–s). The coupling of these corresponding deprotected N-tert-butyloxycarbonyl-L-amino acid amides (4a–s) with dolaproine (5) in the presence of diethylphosphorocyanidate (DEPC) and triethylamine led to the formation of the protected dipeptide amides (6a–s) in appreciable yields as shown in FIG. 3, supra.

The protecting groups of the above mentioned amides (6a–s) were removed with trifluoroacetic acid to afford the corresponding trifluoroacetate salts (7a–s) as shown in FIG. 4, supra. Diethylphosphorocyanidate was used again with excellent results for the coupling of tripeptide trifluoroacetate (TFA, Dov-Val-Dil-OH (8)) with each of the amide salts (7a–s) to yield Dolastatin 10 structural modifications (9a–s) as shown in FIG. 5, supra; and which demonstrate inhibition of cell growth.

All these compounds (9a–s) have demonstrated an outstanding efficacy when administered to human tumor and mouse leukemia cell lines. The various in vitro tests for all these compounds is disclosed hereafter in Table 1.

Accordingly a principal object of the present invention is to provide the elucidation and synthesis of new and novel derivatives of dolastatin 10, each of which exhibits effective activity against various entities in the National Cancer Institute cell line.

Another object of the present invention is to provide new and unique substances which are therapeutically akin to dolastatin 10 and which can be created by economically viable procedures in commercially viable quantities.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

The synthesis of the disclosed compounds involved the use of several General Procedures, which are set forth below, with the use of several amines as a first step the corresponding amines (2a–k) were allowed to react with Boc-L-amino acids (1a–f). The amines were: 4-fluoroaniline (2a); 2-chloroaniline (2b); 3-chloroaniline (2c); 4-chloroaniline (2d); 2,5-dichloroaniline (2e); 4-chlorophenethylamine (2f); 2-amino-6-fluorobenzothiazole (2g); 2-amino-6-chlorobenzothiazole (2h); 2-aminobenzothiazole (2i); 2-aminopyridine (2j); 3-aminoquinoline (2k); and the amino acids were: N-tert-Boc-Methionine (1a); N-tert-Boc-Phenylalanine (1b); N-tert-Boc-Proline (1c); N-tert-Boc-Valine (1d); N-tert-Boc-Isoleucine (1e); N-tert-Boc-p-chloro-Phenylalanine (1f). Synthesis of amides (3a–s) in the presence of 2-ethoxy-1-ethoxycarbonyl-1,2-dihydroquinoline (EEDQ) or isobutylchloroformate or 1,3-dicyclohexylcarbodiimide as condensing agents led to excellent yields. No racemization was observed during these reactions.

General Procedure A

A solution of N-tert-butoxycarbonyl-L-amino acid (1, 10 mmol) in dry tetrahydrofuran (40 mL) was cooled to −15° C. and neutralized with N-methylmorpholine. Isobutylchloroformate (10 mmol) was added, followed, one minute later, by the respective amine 2 (11 mmol). The reaction mixture was allowed to warm up to room temperature. After stirring at room temperature for one hour, THF was removed under reduced pressure and the residue was taken into ethyl acetate (250 mL). The ethyl acetate solution was successively washed with KHSO$_4$ (10%, 2×150 mL), water, saturated sodium bicarbonate (2×150 mL), water and dried (Na$_2$SO$_4$). Treatment with activated carbon and removal of the solvent left behind a residue of the amide which was suitably purified.

General Procedure B

A solution of N-tert-butoxycarbonyl-L-amino acid (1, 10 mmol) in dry tetrahydrofuran (40 mL) was cooled to −15° C. and neutralized with N-methylmorpholine. Isobutylchloroformate (10 mmol) was added, followed, one minute later, by the respective amine 2 (11 mmol). The reaction mixture was allowed to warm up to room temperature. After stirring at room temperature for one hour, the precipitated salt was removed by filtration and the residue was concentrated and crystallized from acetone-hexane to give the crystals of the required amide.

General Procedure C

To a solution of N-tert-butoxycarbonyl-L-amino acid (1, 10 mmol) in dry tetrahydrofuran (20 mL) was added the respective amine 2 (11 mmol) followed by 2-ethoxy-1-ethoxycarbonyl-1,2-dihydroquinoline (EEDQ) (11 mmol) and the solution was stirred for 24 hours at 20° C. The solvent was removed under vacuum at room temperature and the oily product obtained was crystallized from ethyl acetate-hexane to yield the colorless crystals of the required amide.

General Procedure D

In dry tetrahydrofuran (30 mL) were dissolved N-tert-butoxycarbonyl-L-amino acid (1, 10 mmol), the amine 2 (10 mmol), 1-hydroxybenzotriazole (10 mmol) and 1,3-dicyclohexyl-carbodiimide (11 mmol) at 2°–5° C. The reaction mixture stirred at 2°–5° C. for one hour and at 23° C. for one hour. Precipitated dicyclohexylurea was filtered off, solvent removed (reduced pressure) and the residue diluted with ethyl acetate (150 mL). The organic phase was washed with KHSO$_4$ (10%, 40 mL), water (50 mL), saturated aqueous hydrogen carbonate (50 mL) then dried (sodium sulfate). The solvent was removed under reduced pressure and the residue was chromatographed on a SILICA GEL (0.040–0.063 ram) flash column (3.5×22 cm) with hexane-acetone (3:1) as solvent. After the evaporation of solvent from the fractions (selected by thin layer chromatography), the solid was crystallized to yield the pure amide.

General Procedure E

A solution of the N-tert-Boc-amino acid amide (3a, 3c, 3e–g, 3i, 3l–m, 2 mmol) in hydrogen chloride/dioxane (4.0M hydrogen chloride, 10 mL) was stirred at 20° C. for one half hour. Then diethylether (150 mL) was added and the solid obtained was collected by filtration and dried in a vacuum desiccator to afford the respective hydrochloride salt which was used without further purification.

General Procedure F

A solution of the N-tert-Boc-amino acid amide (3h, 3j, 3n, 3p–s, 2 mmol) in hydrogen chloride/acetic acid (1.0M hydrogen chloride, 20 mL) was stirred at 10° C. for one half hour. Then diethylether (150 mL) was added and the solid obtained was collected by filtration and dried in a vacuum desiccator to afford the respective hydrochloride salt which was used without further purification.

General Procedure G

A solution of the N-tert-Boc-amino acid amide (3b and 3o, 2 mmol) in dichloromethane (2 mL) and trifluoroacetic acid (2 mL) was stirred at 10° C. for one half hour. The solvents were removed under reduced pressure and the residue taken into toluene and toluene also removed under reduced pressure. The residue was then dried in a vacuum desiccator to afford the respective trifluoroacetate salt which was used without further purification.

General Procedure H

To a solution of [2S-[2R* (αS*,βS*)]]-1-[(1,1-dimethylethoxy) carbonyl]-β-methoxy-α-methyl-2-pyrrolidine-propanoic acid (N-tert-Boc-Dolaproine, 5, 287 mg, 1 mmol) in dry N,N-dimethylformamide (5 mL) was added the respective amino acid amide hydrogen chloride/ trifluoroacetate salt (4, 1 mmol) followed by triethylamine (2 mmol) and diethyl phosphorocyanidate (DEPC) (1 mmol, ice bath) and the solution was stirred under argon at 0°–5° C. for two hours. The solvent was removed (under vacuum at room temperature) and the residue was diluted with ethyl acetate (100 mL). The organic layer was washed with citric acid (10%, 30 mL), water (30 mL), saturated NaHCO$_3$ solution (30 mL), water (30 mL), then dried (Na$_2$SO$_4$). The solvent was removed under reduced pressure at 40° C. and the residue chromatographed on a SILICA GEL (0.040–0.063 mm) column. After the evaporation of solvent from the fractions (selected by thin layer chromatography), 2 mL dry methylene chloride was added and evaporation was repeated. The residue was dried in a desiccator under vacuum (overnight) to afford the corresponding dipeptide amide (6) as a viscous oil, which was purified from acetone-hexane resulting in colorless solid.

General Procedure I

To a solution of [2S-[2R* (αS,βS,)]]-1-[(1,1-dimethylethoxy) carbonyl]-β-methoxy-α-methyl-2-pyrrolidine-propanoic acid (N-tert-Boc-Dolaproine, 5, 1 mmol) in dry N,N-dimethylformamide (5 mL) was added the respective amino acid amide hydrogen chloride/ trifluoroacetate salt (4, 1 mmol) followed by triethylamine (2 mmol) and DEPC (1 mmol, ice bath) and the solution was stirred under argon at 0°–5° C. for two hours. The solvent was removed (under vacuum at room temperature) and the residue was diluted with ethyl acetate (100 mL). The organic layer was washed with citric acid (10%, 30 mL), water (30 mL), saturated NaHCO$_3$ solution (30 mL), water (30 mL), then dried (Na$_2$SO$_4$). The solvent was removed under reduced pressure at 40° C. The residue was dried in a desiccator under vacuum (overnight) to afford the corresponding dipeptide amide (6) as a solid, which was purified from acetone-hexane resulting in colorless solid.

General Procedure J

To a solution of [2S-[2R* (αS*,βS,)]]-1-[(1,1-dimethylethoxy) carbonyl]-β-methoxy-α-methyl-2-pyrrolidinepropanoic acid (N-tert-Boc-Dolaproine, 5, 1 mmol) in dry methylene chloride (3 mL, distilled from calcium hydride) was added the respective amino acid amide hydrogen chloride salt (4, 1 mmol) followed by triethylamine [2 mmol (for amino acid-3-aminoquinoline salts 3 mmol)] and DEPC (1 mmol, ice bath) and the solution was stirred under argon for two hours. The solvent was removed (under vacuum at room temperature) and the residue was chromatographed on a SILICA GEL (0.040–0.063 mm) column. After the evaporation of solvent from the fractions (selected by thin layer chromatography) 2 mL dry methylene chloride was added and evaporation was repeated. The residue was dried in a desiccator under vacuum (overnight) to afford the corresponding dipeptide amide (6) as a viscous oil, which was precipitated from methylene chloride-hexane resulting in colorless solid.

General Procedure K

A solution of the N-tert-Boc-dipeptide amides 6a–s (1 mmol) in methylene chloride (2 mL) and trifluoroacetic acid (2 mL) was stirred (ice bath under an argon atmosphere) for 30 minutes. The solvent was removed under reduced pressure and toluene was added to the residue. Solvent was again removed in vacuum and this operation was repeated. The residue was dried in a desiccator (under vacuum overnight) to afford the trifluoroacetate salt as a viscous oil, which was used in next step without further purification.

General Procedure L

To a solution of the trifluoroacetate salt (7a–s, 0.2 mmol) in methylene chloride (2 mL, distilled from calcium hydride) was added the Dov-Val-Dil tripeptide trifluoroacetate salt (8, 0.2 mmol) followed by triethylamine (0.63 mmol) and DEPC (0.22 mmol, ice bath). The solution was stirred under argon at 0°–5° C. for one to two hours. The solvent was removed (under vacuum at room temperature) and the residue was chromatographed on a SILICA GEL (0.040–0.063 mm) column. After the evaporation of solvent from the fractions (selected by thin layer chromatography), 2 mL of dry methylene chloride was added followed with 10 mL of n-hexane and the solvents evaporated under a stream of argon to yield a colorless fluffy solid of the required pentapeptide amide (9a–s).

Dolastatin 10 has demonstrated significant in vivo anti-cancer activity as will be shown below but first, let us define our terms.

STATISTICAL DEFINITIONS

The following measures are used to express drug activity by giving the drug dose which reduces cell growth to a specified percentage of growth:

$ED_{50}$ (P-388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage.

TGI, (Total Growth Inhibition), is the drug dose needed to yield zero percent growth, i.e., just as many cells at the end of the experiment as were present in the beginning. Whether just as many cells were killed as were produced (steady state), or no growth occurred (total inhibition), cannot be distinguished.

$LC_{50}$, (Lethal Concentration 50%), is the drug concentration which reduces growth to −50%, i.e., removes half of the cells originally present at the beginning of the experiment.

Each drug is tested at five (5) doses: 100-10-1-0.1-0.01 μg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}>$(highest dose). If no dose yields growth higher than 50% growth, then $ED_{50}<$(lowest dose). Similar calculations are performed for the TGI at 0% growth, and at −50% growth for the $LC_{50}$.

PERCENT OF GROWTH

At the start of an experiment, cells from the in vitro cell cultures are inoculated into the appropriate tubes or microtiter plates. One set of control tubes/plates is immediately counted to determine the number of cells at the start of the experiment. This is the "baseline count", or "$T_{zero}$ reading". At the end of the experiment (48 hours later) a second set of control tubes/plates is analyzed to determine the "Control Growth" value. The growth (or death) of cells relative to the initial quantity of cells is used to define the "Percent of Growth".

| | EXAMPLE:<br>Baseline Count 20<br>Control Count 200<br>(10-Fold Growth) |
|---|---|
| 100% Growth = Control Growth | 100% Growth = 200 |
| 50% Growth = $T_{zero} + \dfrac{Control - T_{zero}}{2}$ | 50% Growth = 110 |
| 0% Growth = $T_{zero}$ | 0% Growth = 20 |
| −50% Growth = $T_{zero}/2$ | −50% Growth = 10 |

Experimental Anti-cancer Activity of Dolastatin 10 in Murine in vivo Systems, T/C (μg/kg)

| |
|---|
| P388 Lymphocytic Leukemia |
| toxic (13.0)<br>155 and 17% cures (6.5)<br>146 and 17% cures (3.25)<br>137 (1.63) |
| L1210 Lymphocytic Leukemia |
| 152 (13)<br>135 (6.5)<br>139 (3.25)<br>120 (1.63) |
| B16 Melanoma |
| 238 and 40% cures (11.11)<br>182 (6.67)<br>205 (4.0)<br>171 (3.4)<br>142 (1.44) |
| M5076 Ovary Sarcoma |
| toxic (26)<br>166 (13)<br>142 (6.5)<br>151 (3.25) |
| LOX Human Melanoma Xenograft to (Nude Mouse) |
| toxic (52)<br>301 and 67% cures (26)<br>301 and 50% cures (13)<br>206 and 33% cures (6.5)<br>170 and 17% cures (3.25) |
| LOX in separate experiments |
| 340 and 50% cures (43)<br>181 and 33% cures (26)<br>192 (15)<br>138 and 17% cures (9.0) |
| Human Mammary Xenograft Nude Mouse |
| Toxic (26)<br>137 (13)<br>178 (6.25) |
| OVCAR-3 Human Ovary Xenograft Nude Mouse |
| 300 (40) |
| MX-1 Human Mammary Xenograft (Tumor Regression) |
| 14 (52)<br>50 (26)<br>61 (13)<br>69 (6.25) |

Dolastatin 10 has also been tested against a minipanel from the NCI Primary screen. These results appear below, showing the amount of dolastatin 10 required to attain $GI_{50}$ in μg/ml, against the cell lines set forth below.

$$\frac{\text{OVCAR-3}}{9.5 \times 10^{-7}} \text{ (A)} \quad \frac{\text{SF 295}}{7.6 \times 10^{-8}} \text{ (B)} \quad \frac{\text{A498}}{2.6 \times 10^{-5}} \text{ (C)}$$

$$\frac{\text{NCI-H460}}{3.4 \times 10^{-6}} \text{ (D)} \quad \frac{\text{KM20L2}}{4.7 \times 10^{-6}} \text{ (E)} \quad \frac{\text{SK-MEL-5}}{7.4 \times 10^{-6}} \text{ (F)}$$

From the foregoing, it can be seen that the in vitro activity of dolastatin 10 in the primary screen has been confirmed by in vivo animal tests.

For the compounds disclosed in this application, the in vitro tests disclosed above are reasonably accurate predictors of anti-cancer activity, and not mere indicators of the desirability for further testing.

All these compounds (9a–s) have demonstrated an outstanding efficacy when used against human cancer and mouse leukemia cell lines. In particular, compound (9d) has shown an unprecedented and extraordinary human tumor inhibiting activity against the Melanoma SK-MEL-5 cell line. The various cancer cell growth inhibitory evaluation for all these compounds is disclosed in Table 1.

TABLE 1

Human Cancer-Cell line and P-388 Mouse Leukemia ($ED_{50}$) data for the pentapeptide amides 9a–s

| | Cell type | Cell line | 9a | 9b | 9c | 9d |
|---|---|---|---|---|---|---|
| GI-50 (μg/ml) | Ovarian | OVCAR-3 | 0.000049 | 0.000028 | 0.000011 | 0.000018 |
| | CNS | SF-295 | 0.0001 | 0.000036 | 0.000031 | 0.000041 |
| | Renal | A498 | 0.00025 | 0.000073 | 0.000084 | 0.00012 |
| | Lung-NSC | NCI-H460 | 0.000089 | 0.000031 | 0.000025 | 0.0000094 |
| | Colon | KM20L2 | 0.00005 | 0.000034 | 0.000023 | 0.000007 |
| | Melanoma | SK-MEL-5 | 0.000038 | 0.00002 | 0.0000013 | $<1.0 \times 10^{-12}$ |
| TGI (μg/ml) | Ovarian | OVCAR-3 | 0.00033 | 0.000091 | 0.0001 | 0.00016 |
| | CNS | SF-295 | >0.001 | >0.001 | >0.001 | >0.001 |
| | Renal | A498 | >0.001 | >0.001 | >0.001 | >0.001 |
| | Lung-NSC | NCI-H460 | 0.00066 | 0.00011 | 0.00011 | 0.00011 |
| | Colon | KM20L2 | 0.00039 | 0.00018 | 0.0001 | 0.00019 |
| | Melanoma | SK-MEL-5 | 0.00057 | >0.001 | 0.00026 | 0.0051 |
| LC-50 (μg/ml) | Ovarian | OVCAR-3 | >0.001 | >0.001 | >0.001 | >0.01 |
| | CNS | SF-295 | >0.001 | >0.001 | >0.001 | >0.01 |
| | Renal | A498 | >0.001 | >0.001 | >0.001 | >0.01 |
| | Lung-NSC | NCI-H460 | >0.001 | >0.001 | >0.001 | >0.01 |
| | Colon | KM20L2 | >0.001 | >0.001 | >0.001 | >0.01 |
| | Melanoma | SK-MEL-5 | >0.001 | >0.001 | >0.001 | >0.01 |
| ED-50 (μg/ml) | Mouse Leukemia | PS-388 | 0.000317 | 0.000211 | 0.00000264 | 0.00258 |

| | Cell type | Cell line | 9e | 9f | 9g | 9h |
|---|---|---|---|---|---|---|
| GI-50 (μg/ml) | Ovarian | OVCAR-3 | 0.00000045 | 0.0000014 | 0.00014 | 0.0000031 |
| | CNS | SF-295 | 0.0000023 | 0.0000025 | 0.00013 | 0.0000036 |
| | Renal | A498 | 0.0000035 | 0.000007 | 0.00036 | 0.000016 |
| | Lung-NSC | NCI-H460 | 0.0000022 | 0.0000018 | 0.00017 | 0.0000029 |
| | Colon | KM20L2 | 0.00000084 | 0.0000029 | 0.00015 | 0.0000042 |
| | Melanoma | SK-MEL-5 | 0.00000033 | 0.0000002 | 0.000062 | 0.0000031 |
| TGI (μg/ml) | Ovarian | OVCAR-3 | 0.0000042 | 0.0000056 | 0.00051 | 0.000017 |
| | CNS | SF-295 | >0.00001 | >0.0001 | >0.001 | >0.0001 |
| | Renal | A498 | >0.00001 | >0.0001 | >0.001 | >0.0001 |
| | Lung-NSC | NCI-H460 | 0.0000085 | 0.00001 | 0.00066 | 0.000012 |
| | Colon | KM20L2 | 0.0000051 | 0.0000084 | 0.00061 | 0.000037 |
| | Melanoma | SK-MEL-5 | >0.00001 | 0.000047 | 0.00065 | >0.0001 |
| LC-50 (μg/ml) | Ovarian | OVCAR-3 | >0.00001 | >0.0001 | >0.001 | >0.0001 |
| | CNS | SF-295 | >0.00001 | >0.0001 | >0.001 | >0.0001 |
| | Renal | A498 | >0.00001 | >0.0001 | >0.001 | >0.0001 |
| | Lung-NSC | NCI-H460 | >0.00001 | >0.0001 | >0.001 | >0.0001 |
| | Colon | KM20L2 | >0.00001 | >0.0001 | >0.001 | >0.0001 |
| | Melanoma | SK-MEL-5 | >0.00001 | >0.0001 | >0.001 | >0.0001 |
| ED-50 (μg/ml) | Mouse Leukemia | PS-388 | 0.000603 | 0.0000452 | 0.000125 | 0.0000482 |

| | Cell type | Cell line | 9i | 9j | 9k | 9l |
|---|---|---|---|---|---|---|
| GI-50 (μg/ml) | Ovarian | OVCAR-3 | 0.000017 | 0.0000031 | 0.0000043 | 0.000018 |
| | CNS | SF-295 | 0.000026 | 0.0000044 | 0.000022 | 0.000036 |
| | Renal | A498 | 0.000067 | 0.000016 | 0.000031 | 0.000059 |
| | Lung-NSC | NCI-H460 | 0.0000032 | 0.0000041 | 0.0000044 | 0.000043 |
| | Colon | KM20L2 | 0.0000048 | 0.0000033 | 0.000022 | 0.000031 |
| | Melanoma | SK-MEL-5 | 0.0000012 | 0.0000013 | 0.000003 | 0.0000061 |
| TGI (μg/ml) | Ovarian | OVCAR-3 | 0.000072 | 0.000012 | 0.000027 | 0.000071 |
| | CNS | SF-295 | >0.001 | >0.0001 | >0.0001 | >0.0001 |
| | Renal | A498 | >0.001 | >0.0001 | >0.0001 | >0.0001 |
| | Lung-NSC | NCI-H460 | 0.000011 | 0.000036 | 0.0000063 | >0.0001 |
| | Colon | KM20L2 | 0.00013 | 0.000013 | 0.000072 | 0.000096 |
| | Melanoma | SK-MEL-5 | 0.00043 | >0.0001 | >0.0001 | >0.0001 |
| LC-50 (μg/ml) | Ovarian | OVCAR-3 | >0.001 | >0.0001 | >0.0001 | >0.0001 |

TABLE 1-continued

Human Cancer-Cell line and P-388 Mouse Leukemia ($ED_{50}$) data for the pentapeptide amides 9a–s

|  | Cell type | Cell line |  |  |  |  |
|---|---|---|---|---|---|---|
|  | CNS | SF-295 | >0.001 | >0.0001 | >0.0001 | >0.0001 |
|  | Renal | A498 | >0.001 | >0.0001 | >0.0001 | >0.0001 |
|  | Lung-NSC | NCI-H460 | >0.001 | >0.0001 | >0.0001 | >0.0001 |
|  | Colon | KM20L2 | >0.001 | >0.0001 | >0.0001 | >0.0001 |
|  | Melanoma | SK-MEL-5 | >0.001 | >0.0001 | >0.0001 | >0.0001 |
| ED-50 (µg/ml) | Mouse Leukemia | PS-388 | 0.000111 | 0.000227 | 0.000383 | 0.000458 |

|  | Cell type | Cell line | 9m | 9n | 9o | 9p |
|---|---|---|---|---|---|---|
| GI-50 (µg/ml) | Ovarian | OVCAR-3 | 0.0000016 | 0.000027 | 0.000032 | 0.00000032 |
|  | CNS | SF-295 | 0.000022 | 0.000035 | 0.00016 | 0.000004 |
|  | Renal | A498 | 0.000016 | 0.000081 | 0.00023 | 0.000008 |
|  | Lung-NSC | NCI-H460 | 0.000011 | 0.000031 | 0.00012 | 0.0000031 |
|  | Colon | KM20L2 | 0.0000041 | 0.000029 | 0.000033 | 0.00000065 |
|  | Melanoma | SK-MEL-5 | 0.0000024 | 0.0000098 | 0.000016 | 0.00000038 |
| TGI (µg/ml) | Ovarian | OVCAR-3 | 0.000011 | 0.000079 | 0.00022 | 0.00001 |
|  | CNS | SF-295 | >0.0001 | >0.0001 | >0.001 | >0.0001 |
|  | Renal | A498 | >0.0001 | >0.0001 | >0.001 | >0.0001 |
|  | Lung-NSC | NCI-H460 | 0.00008 | >0.0001 | 0.00059 | 0.000017 |
|  | Colon | KM20L2 | >0.0001 | >0.0001 | 0.00031 | >0.0001 |
|  | Melanoma | SK-MEL-5 | >0.0001 | >0.0001 | 0.0006 | >0.0001 |
| LC-50 (µg/ml) | Ovarian | OVCAR-3 | >0.0001 | >0.0001 | >0.001 | >0.0001 |
|  | CNS | SF-295 | >0.0001 | >0.0001 | >0.001 | >0.0001 |
|  | Renal | A498 | >0.0001 | >0.0001 | >0.001 | >0.0001 |
|  | Lung-NSC | NCI-H460 | >0.0001 | >0.0001 | >0.001 | >0.0001 |
|  | Colon | KM20L2 | >0.0001 | >0.0001 | >0.001 | >0.0001 |
|  | Melanoma | SK-MEL-5 | >0.0001 | >0.0001 | >0.001 | >0.0001 |
| ED-50 (µg/ml) | Mouse Leukemia | PS-388 | 0.000243 | 0.00083 | 0.000262 | 0.000356 |

|  | Cell type | Cell line | 9q | 9r | 9s |
|---|---|---|---|---|---|
| GI-50 (µg/ml) | Ovarian | OVCAR-3 | 0.000086 | 0.000019 | 0.000018 |
|  | CNS | SF-295 | 0.00036 | 0.000027 | 0.000028 |
|  | Renal | A498 | 0.00041 | 0.000051 | 0.000065 |
|  | Lung-NSC | NCI-H460 | 0.0003 | 0.000026 | 0.000027 |
|  | Colon | KM20L2 | 0.00033 | 0.000031 | 0.00003 |
|  | Melanoma | SK-MEL-5 | 0.00011 | 0.0000057 | 0.0000039 |
| TGI (µg/ml) | Ovarian | OVCAR-3 | >0.0001 | 0.000069 | 0.000079 |
|  | CNS | SF-295 | >0.0001 | >0.0001 | >0.0001 |
|  | Renal | A498 | >0.0001 | >0.0001 | >0.0001 |
|  | Lung-NSC | NCI-H460 | >0.0001 | >0.0001 | >0.0001 |
|  | Colon | KM20L2 | >0.0001 | >0.0001 | >0.0001 |
|  | Melanoma | SK-MEL-5 | >0.0001 | >0.0001 | >0.0001 |
| LC-50 (µg/ml) | Ovarian | OVCAR-3 | >0.0001 | >0.0001 | >0.0001 |
|  | CNS | SF-295 | >0.0001 | >0.0001 | >0.0001 |
|  | Renal | A498 | >0.0001 | >0.0001 | >0.0001 |
|  | Lung-NSC | NCI-H460 | >0.0001 | >0.0001 | >0.0001 |
|  | Colon | KM20L2 | >0.0001 | >0.0001 | >0.0001 |
|  | Melanoma | SK-MEL-5 | >0.0001 | >0.0001 | >0.0001 |
| ED-50 (µg/ml) | Mouse Leukemia | PS-388 | 0.000415 | 0.0041 | 0.00352 |

To further aid in the understanding of the present invention, and not by way of limitation the following examples are presented.

EXAMPLE I

The synthesis of N-tert-butoxycarbonyl-amino acid amides (3a–s) was accomplished by selective use of General Procedures A, B, C, and D, as shown below.

EXAMPLE I-a

Synthesis of N-tert-Butoxycarbonyl-L-Methionine N-4-Fluorophenyl Amide (3a)

Coupling of N-tert-butoxycarbonyl-L-methionine (1a) and 4-fluoroaniline (2a) according to General Procedure A, gave (3a) ($C_{16}H_{23}N_2O_3S_1F_1$, 88%), Rf=0.39 (hexane-acetone 3:1), m.p. 110°–111° C., $[\alpha]_D^{23}$=−33.8° (c 0.6, $CHCl_3$), IR (KBr) v: 449, 461, 500, 519, 565, 685, 725, 752, 777, 812, 837, 870, 918, 961, 1026, 1047, 1099, 1167, 1217, 1254, 1296, 1346, 1368, 1393, 1410, 1443, 1510, 1539, 1557, 1618, 1669, 1888, 1991, 2066, 2363, 2836, 2868, 2920, 2980, 3100, 3162, 3225, 3287, 3567 $cm^{-1}$, $^1H$ NMR ($CDCl_3$) δ: 8.433–8.440 (br s, 1H, Ar—NH), 7.414–7.460 (m, 2H, ArH), 6.940–6.997 (m, 2H, ArH), 5.247–5.275 (br d, 1H, NH), 4.349–4.396 (m, 1H, $H^\alpha$), 2.542–2.651 (m, 2H, $CH_2^\gamma$), 2.199–2.129 (m, 1H, $H^\beta$), 2.099 (s, 3H, $CH_3^\epsilon$), 1.940–2.036 (m, 1H, $H^\beta$), 1.429 (s, 9H, t-Bu); EIMS (70 eV) m/z (%): 342 ($M^+$, 5).

EXAMPLE I-b

Synthesis of N-tert-Butoxycarbonyl-L-Methionine N-2-Chlorophenyl Amide (3b)

Reaction of N-tert-butoxycarbonyl-L-methionine (1a) and 2-chloroaniline (2b) according to General Procedure A, gave after purification on a SILICA GEL column with hexane-acetone (3:1) as the eluent, an oily liquid of (3b) ($C_{16}H_{23}N_2O_3S_1Cl_1$, 79%), Rf=0.43 (hexane-acetone 3:1), $[\alpha]_D^{23}$=−41.5° (c 0.65, $CHCl_3$). IR (KBr) v: 536, 548, 606, 648, 667, 691, 752, 864, 963, 1036, 1055, 1165, 1250, 1298, 1368, 1393, 1441, 1524, 1593, 1616, 1684, 1696, 2338, 2361, 2870, 2920, 2978, 3036, 3061, 3121, 3314 cm$^{-1}$, $^1$H NMR (CDCl$_3$) δ: 8.551 (s, 1H, Ar—NH), 8.321–8.355 (m, 1H, ArH), 7.334–7.336 (m, 1H, ArH), 7.221–7.279 (m, 1H, ArH), 7.005–7.062 (m, 1H, ArH), 5.194–5.214 (br s, 1H, NH), 4.442–4.462 (m, 1H, H$^α$), 2.590–2.638 (m, 2H, CH$_2^γ$), 2.144–2.281 (m, 1H, H$^β$), 2.112 (s, 3H, CH$_3^ε$), 1.966–2.112 (m, 1H, H$^β$), 1.44 (s, 9H, t-Bu); EIMS (70 eV) m/z (%): 358 (M$^+$, 2).

EXAMPLE I-c

Synthesis of N-tert-Butoxycarbonyl-L-Methionine N-3-Chlorophenyl Amide (3c)

Coupling of N-tert-butoxycarbonyl-L-methionine (1a) and 3-chloroaniline (2c) according to General Procedure A, gave after purification on a SILICA GEL column hexane-acetone (3:1) an oily liquid of (3c) (C$_{16}$H$_{23}$N$_2$O$_3$S$_1$Cl$_1$, 94%), Rf=0.40 (hexane-acetone 3:1), [α]$_D^{23}$=−36.8° (c 1.44, CHCl$_3$), IR (KBr) v: 440, 461, 519, 548, 606, 681, 739, 777, 864, 880, 903, 963, 999, 1026, 1049, 1076, 1099, 1165, 1252, 1267, 1300, 1368, 1393, 1427, 1456, 1483, 1506, 1522, 1539, 1595, 1670, 1684, 1697, 2336, 2361, 2868, 2918, 2978, 3061, 3086, 3131, 3198, 3291, 3522, 3545 cm$^{-1}$, $^1$H NMR (CDCl$_3$) δ: 8.472 (br s, 1H, Ar—NH), 7.616–7.629 (m, 1H, ArH), 7.240–7.283 (m, 1H, ArH), 7.153 (dd, 1H, J 7.8 Hz and 8.1 Hz, ArH), 7.023 (d, 1H, J 7.8 Hz, ArH), 5.377 (br s, 1H, NH), 4.407–4.427 (m, 1H, H$^α$), 2.566–2.618 (m, 2H, CH$_2^γ$), 2.116–2.184 (m, 1H, H$^β$), 2.084 (s, 3H, CH$_3^ε$), 1.940–2.070 (m, 1H, H$^β$), 1.425 (s, 9H, t-Bu); EIMS (70 eV) m/z (%): 358 (M$^+$, 2).

EXAMPLE I-d

Synthesis of N-tert-Butoxycarbonyl-L-Phenylalanine N-3-Chlorophenyl Amide (3d)

Condensation of N-tert-butoxycarbonyl-L-phenylalanine (1b) with 3-chloroaniline (20) according to General Procedure D, resulted in (3d) (C$_{20}$H$_{23}$N$_2$O$_3$Cl$_1$, 86%), Rf=0.37 (hexane-acetone 3:1), m.p. 154°–155° C., [α]$_D^{23}$=−18.2° (c 0.45, CHCl$_3$), IR (KBr) v: 440, 496, 565, 606, 621, 679, 694, 731, 775, 856, 882, 903, 999, 1026, 1053, 1080, 1099, 1167, 1223, 1250, 1267, 1294, 1368, 1393, 1425, 1454, 1483, 1497, 1537, 1597, 1669, 2980, 3003, 3032, 3063, 3088, 3135, 3200, 3287 cm$^-$, $^1$H NMR (CDCl$_3$) δ: 8.00 (s, 1H, NH), 7.50–7.01 (m, 9H, 2Ph), 5.13 (m, 1H, NH), 4.45 (m, 1H, CH$^α$), 3.11 (2d, 2H, J 7.2 Hz, CH$_2^β$), 1.39 (s, 9H, t-Bu); EIMS (70 eV) m/z (%): 374 (M$^+$, 4).

EXAMPLE I-e

Synthesis of N-tert-Butoxycarbonyl-L-Methionine N-4-Chlorophenyl Amide (3e)

Condensation of N-tert-butoxycarbonyl-L-methionine (1a) with 4-chloroaniline (2d) according to General Procedure A, resulted in (3e) (C$_{16}$H$_{23}$N$_2$O$_3$S$_1$Cl$_1$, 94%), Rf=0.40 (hexane-acetone 3:1), m.p. 125°–126° C., [α]$_D^{23}$=−32.6° (c 0.73, CHCl$_3$), IR (KBr) v: 473, 509, 540, 644, 673, 719, 762, 828, 868, 924, 963, 1013, 1026, 1047, 1088, 1105, 1117, 1167, 1250, 1285, 1346, 1368, 1402, 1435, 1454, 1495, 1541, 1605, 1667, 1678, 1896, 2793, 2847, 2861, 2918, 2976, 3069, 3127, 3194, 3300 cm$^{-1}$, $^1$H NMR (CDCl$_3$) δ: 8.433–8.449 (br s, 1H, Ar—NH), 7.416–7.466 (m, 2H, ArH), 7.234–7.264 (m, 2H, ArH), 5.175–5.196 (m, 1H, NH), 4.369 (m, 1H, H$^α$), 2.538–2.655 (m, 2H, CH$_2^γ$), 2.134–2.205 (m, 1H, H$^β$), 2.103 (s, 3H, CH$_3^ε$), 1.934–2.031 (m, 1H, H$^β$), 1.434 (s, 9H, t-Bu); EIMS (70 eV) m/z (%): 358 (M$^+$, 4).

EXAMPLE I-f

Synthesis of N-tert-Butoxycarbonyl-L-Phenylalanine N-4-Chlorophenyl Amide (3f)

Condensation of N-tert-butoxycarbonyl-L-phenylalanine (1b) with 4-chloroaniline (2d) according to General Procedure D, resulted in (3f) (C$_{20}$H$_{23}$N$_2$O$_3$Cl$_1$, 84%), Rf=0.44 (hexane-acetone 3:1), [α]$_D^{25}$=+44.1° (c 0.8, CH$_3$OH), M.p. 145°–147° C., IR (KBr) v: 457, 492, 503, 540, 571, 596, 654, 675, 698, 745, 781, 826, 872, 883, 916, 982, 1013, 1034, 1053, 1071, 1088, 1105, 1163, 1223, 1248, 1269, 1287, 1298, 1314, 1366, 1381, 1402, 1454, 1493, 1539, 1601, 1667, 1688, 1707, 2791, 2853, 2864, 2932, 2982, 2999, 3030, 3040, 3057, 3069, 3131, 3200, 3285, 3318, 3430 cm$^{-1}$; $^1$H NMR (CDCl$_3$) δ: 7.84 (s, 1H, NH), 7.32–7.19 (m, 9H, 2Ph), 5.09 (m, 1H, NH), 4.42 (m, 1H, CH$^α$), 3.11 (d, 2H, J 7.2 Hz, CH$_2^β$), 1.39 (s, 9H, t-Bu); EIMS (70 eV) m/z (%): 374 (M$^+$, 5).

EXAMPLE I-g

Synthesis of N-tert-Butoxycarbonyl-L-Methionine N-2,5-Dichlorophenyl Amide (3g)

Reaction of N-tert-butoxycarbonyl-L-methionine (1a) with 2,5-dichloroaniline (2e) according to General Procedure A, gave (3g) (C$_{16}$H$_{22}$N$_2$O$_3$S$_1$Cl$_2$, 98%), Rf=0.48 (hexane-acetone 3:1), m.p. 109°–110° C., [α]$_D^{23}$=−52.1° (c 0.96, CHCl$_3$), IR (KBr) v: 442, 486, 507, 557, 602, 631, 669, 698, 718, 743, 758, 787, 802, 822, 853, 880, 909, 936, 957, 978, 1030, 1059, 1092, 1157, 1167, 1208, 1227, 1262, 1294, 1333, 1368, 1393, 1408, 1425, 1441, 1452, 1522, 1586, 1669, 1705, 2832, 2868, 2905, 2922, 2938, 2980, 3005, 3015, 3077, 3119, 3190, 3347 cm$^{-1}$, $^1$H NMR (CDCl$_3$) δ: 8.653 (s, 1H, Ar—NH), 8.450 (d, 1H, J 2.7 Hz, ArH), 7.240–7.281 (m, 1H, ArH), 6.992–7.029 (m, 1H, ArH), 5.173–5.196 (m, 1H, NH), 4.444 (m, 1H, H$^α$), 2.584–2.634 (m, 2H, CH$_2^γ$), 2.144–2.255 (m, 1H, H$^β$), 2.110 (s, 3H, CH$_3^ε$), 1.959–2.055 (m, 1H, H$^β$), 1.440 (s, 9H, t-Bu); EIMS (70 eV) m/z (%): 392 (M$^+$, 1).

EXAMPLE I-h

Synthesis of N-tert-Butoxycarbonyl-L-Phenylalanine N-2,5-Dichlorophenyl Amide (3h)

Condensation of N-tert-butoxycarbonyl-L-Phenylalanine (1b) with 2,5-dichloroaniline (2e) according to General Procedure A, resulted in (3h) (C$_{20}$H$_{22}$N$_2$O$_3$Cl$_2$, 82%), Rf=0.52 (hexane-acetone 3:1), [α]$_D^{25}$=−21.9° (c 0.81, CH$_2$OH), m.p. 127°–128° C., IR (KBr) v: 440, 498, 513, 554, 565, 583, 662, 700, 719, 741, 754, 781, 795, 853, 874, 889, 909, 972, 1024, 1038, 1057, 1090, 1159, 1200, 1215, 1260, 1271, 1294, 1308, 1323, 1368, 1393, 1408, 1449, 1460, 1516, 1586, 1669, 1707, 2853, 2936, 2982, 3009, 3038, 3067, 3119, 3165, 3287, 3320, 3374 cm$^{-1}$; $^1$H NMR (CDCl$_3$) δ: 8.30 (s, 1H, NH), 8.5–8.4 7.33–6.97 (m, 8H, 2Ph), 4.96 (m, 1H, NH), 4.5 (m, 1H, CH$^α$), 3.16 (d, 2H, J 6.6 Hz, CH$_2^β$), 1.4 (s, 9H, t-Bu); EIMS (70 eV) m/z (%): 408 (M$^+$, 2).

EXAMPLE I-i

Synthesis of N-tert-Butoxycarbonyl-L-Methionine N-1-(2-p-Chlorophenylethyl) Amide (3i)

Condensation of N-tert-butoxycarbonyl-L-methionine (1a) with 4-chlorophenethylamine (2f) according to General Procedure B, resulted in (3i) (C$_{16}$H$_{22}$N$_2$O$_3$S$_1$Cl$_2$, 78%), Rf=0.32 (hexane-acetone 3:1), m.p. 130°–132° C., [α]$_D^{23}$=−10.3° (c 0.79, CHCl$_3$), IR (KBr) v: 434, 465, 502, 534, 552, 629, 681, 702, 743, 754, 779, 802, 826, 856, 895, 909, 924, 955, 974, 1017, 1026, 1049, 1086, 1107, 1175, 1236, 1246, 1292, 1308, 1331, 1350, 1371, 1395, 1406, 1445, 1491, 1526, 1657, 1680, 1844, 1869, 1896, 1908, 2338, 2363, 2787, 2836, 2868, 2930, 2982, 3019, 3065, 3081, 3318, 3337 cm$^{-1}$, $^1$H NMR (CDCl$_3$) 7.240–7.275 (m, 2H, ArH), 7.079–7.123 (m, 2H, ArH), 6.175 (s, H, Ar—NH), 5.057–5.077 (m, 1H, NH), 4.156 (dd, 1H, J 14.4 & 7.2 Hz, H$^α$), 3.414–3.523 (m, 2H, N—CH$_2$), 2.762 (t, 2H, J 7.2 Hz, Ar—CH$_2$), 2.368–2.547 (m, 2H, CH$_2^γ$), 2.053 (s, 3H, CH$_3^ε$), 1.962–2.031 (m, 1H, H$^β$), 1.809–1.903 (m, 1H, H$^β$), 1.401 (s, 9H, t-Bu); EIMS (70 eV) m/z (%): 386 (M$^+$, 2).

EXAMPLE I-j
Synthesis of N-tert-Butoxycarbonyl-L-Phenylalanine N-2-(6-Fluoro)benzothiazole Amide (3j)

Condensation of N-tert-butoxycarbonyl-L-phenylalanine (1b) with 3-chloroaniline (2g) according to General Procedure D, resulted in (3j) ($C_{21}H_{22}N_3O_3S_1F_1$, 92%), Rf=0.39 (hexane-acetone 3:1); $[\alpha]_D^{25}$=+50.7° (c 0.73, $CH_3OH$), M.p. 183°–185° C., IR (KBr) v: 426, 446, 471, 505, 542, 569, 611, 650, 667, 704, 733, 745, 793, 814, 828, 855, 883, 912, 943, 995, 1024, 1044, 1080, 1165, 1200, 1225, 1250, 1290, 1319, 1366, 1375, 1441, 1460, 1499, 1539, 1555, 1611, 1670, 1715, 2635, 2718, 2729, 2810, 2857, 2922, 2978, 3009, 3030, 3046, 3088, 3268, 3412 $cm^{-1}$; $^1H$ NMR ($CDCl_3$) δ: 7.70–7.10 (m, 8H, 2Ph), 4.9 (m, 1H, NH), 4.64 (m, 1H, $CH^\alpha$), 3.27–3.07 (m, 2H, $CH_2^\beta$), 1.38 (s, 9H, t-Bu); EIMS (70 eV) m/z (%): 415 ($M^+$, 6).

EXAMPLE I-k
Synthesis of N-tert-Butoxycarbonyl-L-Phenylalanine N-2-(6-Chloro)benzothiazole Amide (3k)

Condensation of N-tert-butoxycarbonyl-L-phenylalanine (1b) with 2-amino-6-chlorobenzothiazole (2h) according to General Procedure D, resulted in (3k) ($C_{21}H_{22}N_3O_3S_1Cl_1$, 85%), Rf=0.42 (hexane-acetone 3:1); $[\alpha]_D^{25}$=+53.8° (c 0.7, $CH_3OH$), M.p. 187°–188° C., IR (KBr) v: 463, 482, 496, 529, 554, 571, 592, 621, 698, 727, 748, 762, 783, 833, 856, 870, 920, 964, 991, 1017, 1045, 1080, 1098, 1126, 1169, 1202, 1240, 1275, 1314, 1366, 1391, 1451, 1503, 1545, 1597, 1674, 1696, 1707, 2814, 2864, 2932, 2978, 3019, 3030, 3063, 3086, 3144, 3231, 3349, 3387, 3407 $cm^{-1}$; $^1H$ NMR ($CDCl_3$) δ: 7.77–7.13 (m, 8H, 2Ph), 4.99 (m, 1H, NH), 4.64 (m, 1H, $CH^\alpha$), 3.26–3.07 (m, 2H, $CH_2^\beta$), 1.38 (s, 9H, t-Bu); EIMS (70 eV) m/z (%): 431 ($M^+$, 9).

EXAMPLE I-l
Synthesis of N-tert-Butoxycarbonyl-L-(p-Chloro) Phenylalanine N-2-(6-Chloro)benzothiazole Amide (3l)

Condensation of N-tert-butoxycarbonyl-L-(p-chloro) phenylalanine (1f) with 2-amino-6-chlorobenzothiazole (2h) according to General Procedure D, resulted in (3l) ($C_{21}H_{21}N_3O_3S_1Cl_2$, 78%), Rf=0.43 (hexane-acetone 3:1), $[\alpha]_D^{25}$=+61.6° (c 0.38, $CH_3OH$), M.p. 200°–201° C., IR (KBr) v: 467, 492, 536, 583, 594, 621, 665, 698, 739, 762, 785, 797, 816, 835, 858, 868, 899, 963, 993, 1017, 1045, 1094, 1128, 1167, 1200, 1242, 1275, 1317, 1352, 1368, 1391, 1410, 1449, 1499, 1545, 1595, 1626, 1676, 1696, 1707, 2853, 2932, 2980, 3011, 3065, 3086, 3183, 3351, 3385, 3405 $cm^{-1}$; $^1H$ NMR ($CDCl_3$) δ: 7.77–7.01 (m, 7H, 2Ph), 5.02 (m, 1H, NH), 4.64 (m, 1H, $CH^\alpha$), 3.25–3.02 (m, 2H, $CH_2^\beta$), 1.39 (s, 9H, t-Bu); EIMS (70 eV) m/z (%): 465 ($M^+$, 7).

EXAMPLE I-m
Synthesis of N-tert-Butoxycarbonyl-L-Methionine N-2-Benzothiazole Amide (3m)

Condensation of N-tert-butoxycarbonyl-L-methionine (1a) with 2-aminobenzothiazole (2i) according to General Procedure C, resulted in (3m) ($C_{17}H_{23}N_3O_3S_2$, 48%), Rf=0.62 (hexane-acetone 3:2), $[\alpha]_D^{25}$=−35.2° (c 0.69, $CH_3OH$), M.p. 155.5°–156.1° C., IR (KBr) v: 438, 469, 509, 527, 546, 569, 615, 654, 689, 704, 714, 729, 760, 816, 870, 926, 939, 953, 972, 1013, 1026, 1051, 1169, 1211, 1252, 1267, 1285, 1298, 1316, 1343, 1368, 1393, 1441, 1454, 1524, 1599, 1678, 1701, 2728, 2778, 2828, 2913, 2928, 2949, 2978, 2999, 3013, 3067, 3098, 3262 $cm^{-1}$; $^1H$ NMR ($CDCl_3$) δ: 7.82–7.28 (m, 4H, Ar—H), 5.33 (bs, 1H, NH—Met), 4.59 (m, 1H, $H^\alpha$—Met), 2.59 (m, 2H, $CH_2^\gamma$), 2.31–2.19 (m, 1H, $CH^\gamma$), 2.11–1.97 (m, 1H, $CH^\beta$), 2.07 (s, 3H, S—Me), 1.45 (s, 9H, t-Bu); EIMS m/z (%): 381 ($M^+$, 21).

EXAMPLE I-n
Synthesis of N-tert-Butoxycarbonyl-L-Proline N-2-Benzothiazole Amide (3n)

Reaction of N-tert-butoxycarbonyl-L-proline (10) with 2-aminobenzothiazole (2i) according to General Procedure C, gave (3n) ($C_{17}H_{21}N_3O_3S$, 57%), Rf=0.58 (hexane-acetone 3:2), $[\alpha]_D^{25}$=−63.7° (c 0.86, $CH_3OH$), M.p. 163.6°–164.8° C., IR (KBr) v: 436, 519, 540, 588, 640, 664, 704, 731, 756, 777, 853, 868, 880, 891, 909, 930, 970, 1001, 1017, 1028, 1047, 1069, 1092, 1125, 1167, 1225, 1263, 1292, 1314, 1346, 1368, 1393, 1427, 1478, 1497, 1557, 1601, 1651, 1721, 1750, 2851, 2880, 2930, 2974, 2990, 3057, 3067, 3140, 3185, 3208, 3283, 3325 $cm^{-1}$; $^1H$ NMR ($CDCl_3$) δ: 7.81–7.24 (m, 4H, Ar—H), 4.60–4.35 (m, 1H, $H^\alpha$-Pro), 3.60–3.36 (m, 2H, $CH_2^\delta$-Pro), 4.11–3.81 (m, 2H, $H^\alpha$-Pro, CH-Dap), 2.51–2.14 (bs, 1H, NH-BnThz), 2.05–1.90 (m, 2H, $CH_2$), 1.65–1.70 (m, 2H, $CH_2$), 1.47 (s, 9H, t-Bu); EIMS m/z (%): 347 ($M^+$, 33).

EXAMPLE I-o
Synthesis of N-tert-Butoxycarbonyl-L-Methionine N-2-Pyridyl Amide (3o)

Condensation of N-tert-butoxycarbonyl-L-inethionine (1a) with 2-aminopyridine (2j) according to General Procedure A, resulted, after purification on a SILICA GEL column (hexane-acetone 3:1), in (3o) ($C_{15}H_{23}N_3O_3S_1$, 62%), Rf=0.33 (hexane-acetone 3:1), m.p. 135°–137° C., $[\alpha]_D^{23}$= −28.2° (c 0.11, $CHCl_3$), IR (KBr) v: 432, 459, 471, 496, 527, 623, 681, 737, 775, 829, 847, 864, 924, 964, 999, 1028, 1053, 1099, 1165, 1252, 1283, 1304, 1366, 1389, 1435, 1462, 1532, 1580, 1603, 1674, 1711, 2363, 2832, 2915, 2953, 2974, 2999, 3046, 3127, 3262 $cm^{-1}$, $^1H$ NMR ($CDCl_3$) δ: 8.647–8.655 (br s, 1H, Ar—NH), 8.264–8.290 (m, 1H, ArH), 8.1705 (d, 1H, J 8.1 Hz, ArH), 7.659–7.718 (m, 1H, ArH), 7.016–7.055 (m, 1H, ArH), 5.210–5.227 (m, 1H, NH), 4.440 (m, 1H, $H^\alpha$), 2.540–2.638 (m, 2H, $CH_2^\gamma$), 2.138–2.253 (m, 1H, $H^\beta$), 2.099 (s, 3H, $CH_3^\epsilon$), 1.968–2.040 (m, 1H, $H^\beta$), 1.436 (s, 9H, t-Bu); EIMS (70 eV) m/z (%): 325 ($M^+$, 5).

EXAMPLE I-p
Synthesis of N-tert-Butoxycarbonyl-L-Methionine N-3-Quinoline Amide (3p)

Condensation of N-tert-butoxycarbonyl-L-inethionine (1a) with 3-aminoquinoline (2k) according to General Procedure C, gave an oily liquid of (3p) ($C_{19}H_{25}N_3O_3S$, 56%), Rf=0.47 (hexane-acetone 3:2), $[\alpha]_D^{25}$=−40.6° (c 0.47, $CH_3OH$), IR (KBr) ρ: 476, 567, 613, 642, 667, 687, 750, 783, 808, 860, 901, 957, 990, 1024, 1047, 1165, 1233, 1285, 1302, 1346, 1368, 1391, 1424, 1456, 1470, 1491, 1506, 1522, 1541, 1559, 1580, 1615, 1674, 1684, 1697, 2870, 2918, 2976, 3001, 3036, 3057, 3088, 3291, 3486, 3505, 3567, 3588 $cm^{-1}$; $^1H$ NMR ($CDCl_3$) δ: 9.02 (bs, 1H, NH-Quinoline), 8.80 (s, 1H, Ar—H), 8.77 (s, 1H, Ar—H), 8.06–7.50 (m, 4H, Ar—H), 5.26 (d, J 8.3 Hz, 1H, NH—Met), 4.47 (m, 1H, $H^\alpha$—Met), 2.70–2.60 (m, 2H, $CH_2^\gamma$), 2.31–1.98 (m, 2H, $CH_2^\beta$), 2.13 (s, 3H, S—Me), 1.46 (s, 9H, t-Bu); EIMS m/z (%): 375 ($M^+$, 17).

EXAMPLE I-q
Synthesis of N-tert-Butoxycarbonyl-L-Proline N-3-Quinoline Amide (3q)

Coupling of N-tert-butoxycarbonyl-L-proline (1c) and 3-aminoquinoline (2k) according to General Procedure C, produced (3q) ($C_{19}H_{23}N_3O_3$, 54%), Rf=0.40 (hexane-acetone 3:2), $[\alpha]_D^{25}$=−106.8° (c 0.41, $CH_3OH$), M.p. 199.8°–200.2° C., IR (KBr) v: 434, 475, 500, 527, 540, 586, 611, 696, 756, 772, 785, 855, 883, 905, 920, 959, 990, 1018, 1092, 1126, 1159, 1194, 1217, 1242, 1254, 1275, 1312, 1344, 1362, 1391, 1418, 1447, 1456, 1478, 1493, 1557, 1580, 1669, 1703, 1829, 2363, 2874, 2932, 2953, 2974, 3052, 3094, 3127, 3163, 3189, 3254, 3300 cm$^{-1}$; $^1$H NMR (CDCl$_3$) δ: 10.07 (bs, 1H, NH-Quinoline), 8.70 (s, 2H, Ar—H), 8.00–7.45 (m, 4H, Ar—H), 4.53 (m, 1H, H$^α$-Pro), 3.46–3.36 (m, 2H, CH$_2$$^δ$), 2.04–1.91 (m, 4H, CH$_2$$^β$, CH$_2$$^γ$), 1.49 (s, 9H, t-Bu); EIMS m/z (%): 341 (M$^+$, 21).

EXAMPLE I-r

Synthesis of N-tert-Butoxycarbonyl-L-Valine N-3-Quinoline Amide (3r)

Coupling of N-tert-butoxycarbonyl-L-valine (1d) and 3-aminoquinoline (2k) according to General Procedure C, gave (3r) (C$_{19}$H$_{25}$N$_3$O$_3$, 61%) , Rf=0.51 (hexane-acetone 3:2) , [α]$_D$$^{25}$=–47.7° (c 0.92, CH$_3$OH), M.p. 181.6°–182.7° C., IR (KBr) v: 436, 476, 581, 598, 619, 681, 729, 756, 783, 870, 905, 932, 961,. 990, 1009, 1040, 1096, 1167, 1213, 1250, 1283, 1323, 1346, 1364, 1398, 1422, 1470, 1495, 1555, 1580, 1682, 1707, 1807, 1819, 2874, 2899, 2934, 2972, 3007, 3054, 3094, 3133, 3225, 3248, 3304 cm$^{-1}$; $^1$H NMR (CDCl$_3$) δ: 8.99 (bs, 1H, NH-Quinoline), 8.69 (bs, 1H, Ar—H), 8.64 (s, 1H, Ar—H), 7.93–7.38 (m, 4H, Ar—H), 5.26 (d, J 8.3 Hz, 1H, NH-Val), 4.14 (m, 1H, H$^α$-Val), 2.28–2.21 (m, 1H, CH$^β$), 1.46 (s, 9H, t-Bu), 1.03 (m, 6H, Me$^{x,y}$-Val); EIMS m/z (%): 343 (M$^+$, 20).

EXAMPLE I-s

Synthesis of N-tert-Butoxycarbonyl-L-Isoleucine N-3-Quinoline Amide (3s)

Reaction of N-tert-butoxycarbonyl-L-isoleucine (1e) and 3-aminoquinoline (2k) according to General Procedure C, resulted in (3s) (C$_{20}$H$_{27}$N$_3$O$_3$, 58%), Rf=0.54 (hexane-acetone 3:2), [α]$_D$$^{25}$=–40.0° (c 0.57, CH$_3$OH), M.p. 163.5°–164.1° C., IR (KBr) v: 422, 444, 476, 534, 581, 617, 692, 733, 756, 783, 820, 862, 905, 941, 961, 988, 1011, 1018, 1042, 1090, 1167, 1192, 1211, 1236, 1254, 1289, 1312, 1346, 1364, 1395, 1420, 1468, 1493, 1553, 1580, 1682, 2685, 2878, 2891, 2936, 2974, 3009, 3038, 3088, 3214, 3243, 3300 cm$^{-1}$; $^1$H NMR (CDCl$_3$) δ: 8.98 (bs, 1H, NH-Quinoline), 8.69 (m, 2H, Ar—H), 7.93–7.39 (m, 4H, Ar—H), 5.23 (d, J 8.9 Hz, 1H, NH-Ile), 4.18 (m, 1H, H$^α$-Ile), 2.14–1.96 (m, 2H, CH$_2$$^γ$), 1.66–1.58 (m, 1H, CH$^β$), 1.45 (s, 9H, t-Bu), 1.03–0.89 (m, 6H, Me$^β$-Ile , Me$^δ$-Ile); EIMS m/z (%): 357 (M$^+$, 15).

EXAMPLE II-a

Synthesis of N-tert-Butoxycarbonyl-(S,R,R)-Dolaproinyl-L-Methionine N-4-Fluorophenyl Amide (6a)

Reaction of N-tert-Boc-dolaproine (5) with the methionine amide hydrochloride (4a) followed by chromatography (hexane-acetone 3:1) according to General Procedure H, gave the Boc-dipeptide amide (6a) (C$_{25}$H$_{38}$N$_3$O$_5$S$_1$F$_1$, 77%), Rf=0.27 (hexane-acetone 3:1), m.p. 205°–210° C., [α]$_D$$^{23}$=–67.8° (c 0.46, CHCl$_3$), IR (KBr) v: 471, 496, 517, 546, 598, 696, 775, 806, 833, 860, 895, 922, 951, 974, 1017, 1038, 1065, 1111, 1169, 1215, 1256, 1298, 1312, 1337, 1366, 1400, 1456, 1478, 1512, 1541, 1634, 1686, 1844, 1869, 1881, 1917, 2363, 2834, 2880, 2932, 2980, 3071, 3158, 3221, 3270, 3302 cm$^{-1}$, $^1$H NMR (CDCl$_3$) δ: 8.583, 8.847 (br s, 1H, Ar—NH), 7.409–7.453 (m, 2H, ArH), 7.105–7.147, 6.520 (m, 1H, NH), 6.933–6.979 (m, 2H, ArH), 4.627–4.690 (m, 1H, H$^α$), 3.781–3.884 (m, 2H, N—CH, CH—OCH$_3$), 3.416 (s, 3H, OCH$_3$), 3.538–3.192 (m, 2H, N—CH$_2$), 2.547–2.705 (m, 2H, CH$_2$$^γ$) 2.430–2.497 (m, 1H, CH—CH$_3$) 1.62–2.35 (m, 6H, CH$_2$$^β$, CH$_2$—CH$_2$), 2.112 (s, 3H, CH$_3$$^ε$), 1.405, 1.425 (s, 9H, t-Bu), 1.275 (m, 3H, CH$_3$); EIMS (70 eV) m/z (%): 511 (M$^+$, 0.52).

EXAMPLE II-b

Synthesis of N-tert-Butoxycarbonyl-(S,R,R)-Dolaproinyl-L-Methionine N-2-Chlorophenyl Amide (6b)

Reaction of N-tert-Boc-dolaproine (5) with the methionine amide trifluoroacetate (4b) followed by chromatography (hexane-acetone 3:2) according to General Procedure H, gave the Boc-dipeptide amide (6b) (C$_{25}$H$_{38}$N$_3$O$_5$S$_1$Cl$_1$, 74%), Rf=0.31 (hexane-acetone 3:1), m.p. 112°–114° C., [α]$_D$$^{23}$=–76.2° (c 0.21, CHCl$_3$), IR (KBr) v: 488, 521, 544, 575, 615, 689, 750, 775, 820, 864, 893, 922, 957, 974, 1005, 1036, 1063, 1107, 1134, 1173, 1242, 1287, 1308, 1321, 1339, 1366, 1391, 1443, 1479, 1530, 1588, 1634, 1690, 1869, 2834, 2876, 2932, 2974, 3046, 3119, 3225, 3256, 3312 cm$^{-1}$, $^1$H NMR (CDCl$_3$) δ: 8.575, 8.716 (br s, 1H, Ar—NH), 8.197–8.286 (m, 1H, ArH), 7.327–7.381 (m, 1H, ArH), 7.207–7.262 (m, 1H, ArH), 7.001–7.049 (m, 1H, ArH), 7.2, 6.542 (m, 1H, NH), 4.7–4.4.82 (m, 1H, H$^α$), 3.7–3.95 (m, 2H, N—CH, CH—OCH$_3$), 3.422 (s, 3H, OCH$_3$), 3.2–3.6 (m, 2H, N—CH$_2$), 2.6–2.7 (m, 2H, CH$_2$$^γ$), 2.4–2.5 (m, 1H, CH—CH$_3$), 1.65–2.3 (m, 6H, CH$_2$$^β$, CH$_2$—CH$_2$), 2.118 (s, 3H, CH$_3$$^ε$), 1.388, 1.460 (s, 9H, t-Bu), 1.270 (m, 3H, CH$_3$); EIMS (70 eV) m/z (%): 527 (M$^+$, 0.70).

EXAMPLE II-c

Synthesis of N-tert-Butoxycarbonyl-(S,R,R)-Dolaproinyl-L-Methionine N-3-Chlorophenyl Amide (6c)

Reaction of N-tert-Boc-dolaproine (5) with the methionine amide hydrochloride (4c) followed by chromatography (hexane-acetone 1:1) according to General Procedure H, gave the Boc-dipeptide amide (6c) (C$_{25}$H$_{38}$N$_3$O$_5$S$_1$Cl$_1$, 88%), Rf=0.29 (hexane-acetone 3:1), m.p. 140°–145° C., [α]$_D$$^{23}$=–67.5° (c 0.64, CHCl$_3$), IR (KBr) v: 440, 486, 521, 532, 554, 575, 592, 617, 685, 775, 878, 899, 920, 961, 974, 999, 1065, 1113, 1140, 1171, 1244, 1310, 1366, 1393, 1454, 1481, 1539, 1595, 1636, 1684, 1844, 1869, 2361, 2834, 2878, 2932, 2976, 3059, 3129, 3192, 3258, 3308, 3567 cm$^{-1}$, $^1$H NMR (CDCl$_3$) δ: 9.018, 8.810 (s, 1H, Ar—NH), 7.612–7.623, 6.581–6.570 (m, 1H, NH), 7.547 (s, 1H, ArH), 7.104–7.351 (m, 3H, ArH), 4.638–4.660 (m, 1H, H$^α$), 3.772–3.886 (m, 2H, N—CH, CH—OCH$_3$), 3.423 (s, 3H, OCH$_3$), 3.184–3.6 (m, 2H, N—CH$_2$), 2.609–2.677 (m, 2H, CH$_2$$^γ$) 2.403–2.499 (m, 1H, CH—CH$_3$), 1.65–2.3 (m, 6H, CH$_2$$^β$, CH$_2$—CH$_2$), 2.107 (s, 3H, CH$_3$$^ε$), 1.412, 1.436 (s, 9H, t-Bu), 1.259 (m, 3H, CH$_3$); EIMS (70 eV) m/z (%): 527 (M$^+$, 0.67).

EXAMPLE II-d

Synthesis of N-tert-Butoxycarbonyl-(S,R,R)-Dolaproinyl-L-Phenylalanine N-3-Chlorophenyl Amide (6d)

Reaction of N-tert-Boc-dolaproine (5) with the phenylalanine amide hydrochloride (4d) followed by chromatography (hexane-acetone 3:1) according to General Procedure H, gave the Boc-dipeptide amide (6d) (C$_{29}$H$_{38}$N$_3$O$_5$Cl$_1$, 86%), Rf=0.29 (hexane-acetone 3:1), m.p. 152°–153° C., [α]$_D$$^{23}$=–69.5° (c 0.43, CHCl$_3$), IR (KBr) v: 446, 465, 490, 503, 532, 559, 581, 669, 681, 698, 748, 774, 870, 901, 918, 966, 1001, 1034, 1063, 1107, 1165, 1231, 1248, 1296, 1308, 1323, 1339, 1366, 1406, 1454, 1481, 1537, 1595, 1642, 1686, 2826, 2878, 2938, 2974, 3027, 3059, 3081, 3127, 3190, 3275, 3295, 3335 cm$^{-1}$; $^1$H NMR (CDCl$_3$) δ: 7.50–6.93 (m, 9H, 2Ph), 4.76 (m, 1H, PheCH$^α$), 3.81–3.40 (m, 2H), 3.34 (s, 3H, OMe), 3.30–3.00 (m, 4H), 2.35–2.30 (m, 1H), 1.90–1.50 (m, 6H), 1.41 (s, 9H, t-Bu), 1.09 (d, 3H, Me); EIMS (70 eV) m/z (%): 513 (M$^+$, 2).

EXAMPLE II-e

Synthesis of N-tert-Butoxycarbonyl-(S,R,R)-Dolaproinyl-L-Methionine N-4-Chlorophenyl Amide (6e)

Reaction of N-tert-Boc-dolaproine (5) with the methionine amide hydrochloride (4e) according to General Procedure I, gave the Boc-dipeptide amide (6e) (C$_{25}$H$_{38}$N$_3$O$_5$S$_1$Cl$_1$, 93%), Rf=0.29 (hexane-acetone 3:1), m.p. 220°–225° C., [α]$_D$$^{23}$=–71.7° (c 0.42, CHCl$_3$), IR (KBr) v: 424, 509, 546, 579, 596, 681, 696, 774, 829, 845, 866, 895, 922, 951, 964, 974, 1015, 1038, 1065, 1109, 1171, 1252, 1287, 1310, 1339, 1366, 1402, 1454, 1495, 1541, 1597, 1634, 1686, 1771, 1844, 1883, 1927, 2336, 2361, 2834, 2878, 2932, 2980, 3061, 3123, 3190, 3258, 3291, 3308 cm$^{-1}$, $^1$H NMR (CDCl$_3$) δ: 8.947, 8.714 (s, 1H, Ar—NH), 7.205–7.468 (m, 4H, ArH), 7.233, 6.53–6.58 (m, 1H, NH), 4.638–4.660 (m, 1H, H$^α$), 3.770–3.883 (m, 2H, N—CH, CH—OCH$_3$), 3.414 (s, 3H, OCH$_3$), 3.184–3.6 (m, 2H, N—CH$_2$), 2.6–2.7 (m, 2H, CH$_2$$^γ$), 2.4–2.5 (m, 1H, CH—CH$_3$), 1.65–2.3 (m, 6H, CH$_2$$^β$, CH$_2$—CH$_2$), 2.105 (s, 3H, CH$_3$$^ε$), 1.416 (s, 9H, t-Bu), 1.247 (m, 3H, CH$_3$); EIMS (70 eV) m/z (%): 527 (M$^+$, 0.48).

EXAMPLE II-f
Synthesis of N-tert-Butoxycarbonyl-(S,R,R)-Dolaproinyl-L-Phenylalanine N-4-Chlorophenyl Amide (6f)

Reaction of N-tert-Boc-dolaproine (5) with the phenylalanine amide hydrochloride (4f) followed by chromatography (hexane-acetone 3:2) according to General Procedure H, gave the Boc-dipeptide amide (6f) (C$_{29}$H$_{38}$N$_3$O$_5$S$_1$, 78%), Rf=0.31 (hexane-acetone 3:1), [α]$_D$$^{25}$=−31.1° (c 0.35, CH$_3$OH), M.p. 188°–190° C., IR (KBr) v: 463, 500, 540, 556, 575, 596, 673, 698, 741, 774, 826, 866, 889, 922, 974, 1013, 1034, 1042, 1065, 1103, 1171, 1211, 1248, 1269, 1289, 1308, 1339, 1366, 1400, 1456, 1493, 1545, 1609, 1643, 1694, 1782, 1885, 1946, 2837, 2880, 2934, 2976, 3032, 3065, 3127, 3196, 3298 cm$^{-1}$; $^1$H NMR (CDCl$_3$) δ: 7.38–7.19 (m, 9H, 2Ph), 4.70 (m, 1H, PheCH$^α$), 3.80–3.40 (m, 2H), 3.34 (s, 3H, OMe), 3.30–3.07 (m, 4H), 2.35–2.30 (m, 1H), 1.90–1.50 (m, 6H), 1.42 (s, 9H, t-Bu), 1.1 (d, 3H, Me); EIMS (70 eV) m/z (%): 543 (M$^+$, 0.26).

EXAMPLE II-g
Synthesis of N-tert-Butoxycarbonyl-(S,R,R)-Dolaproinyl-L-Methionine N-2,5-Dichlorophenyl Amide (6g)

Reaction of N-tert-Boc-dolaproine (5) with the methionine amide hydrochloride (4g) according to General Procedure I, gave the Boc-dipeptide amide (6g) (C$_{25}$H$_{37}$N$_3$O$_5$S$_1$Cl$_2$, 77%), Rf=0.35 (hexane-acetone 3:1), m.p. 125°–130° C., [α]$_D$$^{23}$=−73.2° (c 0.57, CHCl$_3$), IR (KBr) v: 446, 554, 586, 613, 625, 662, 671, 739, 774, 808, 868, 914, 972, 1032, 1096, 1167, 1262, 1368, 1402, 1454, 1478, 1524, 1584, 1655, 1690, 2834, 2880, 2934, 2976, 3065, 3102, 3304, 3493 cm$^{-1}$, $^1$H NMR (CDCl$_3$) δ: 8.840, 8.721 (s, 1H, Ar—NH), 8.340–8.407 (m, 1H, ArH), 7.416–7.434, 6.557 (m, 1H, NH), 7.251 (d, J 6.6 Hz, 1H, ArH), 6.996 (d, J 8.1 Hz, 1H, ArH), 4.709–4.733 (m, 1H, H$^α$), 3.694–3.957 (m, 2H, N—CH, CH—OCH$_3$), 3.414, 3.459 (s, 3H, OCH$_3$), 3.196–3.564 (m, 2H, N—CH$_2$), 2.6–2.7 (m, 2H, CH$_2$$^γ$), 2.4–2.5 (m, 1H, CH—CH$_3$), 1.65–2.3 (m, 6H, CH$_2$$^β$, CH$_2$—CH$_2$), 2.109 (s, 3H, CH$_3$$^ε$), 1.396, 1.401 (s, 9H, t-Bu), 1.262 (m, 3H, CH$_3$); EIMS (70 eV) m/z (%): 561 (M$^+$, 0.80).

EXAMPLE II-h
Synthesis of N-tert-Butoxycarbonyl-(S,R,R)-Dolaproinyl-L-Phenylalanine N-2,5-Dichlorophenyl Amide (6h)

Reaction of N-tert-Boc-dolaproine (5) with the phenylalanine amide hydrochloride (4h) followed by chromatography (hexane-acetone 3:2) according to General Procedure H, gave the Boc-dipeptide amide (6h) (C$_{29}$H$_{37}$N$_3$O$_5$Cl$_2$, 86%), Rf=0.38 (hexane-acetone 3:1), [α]$_D$$^{25}$=−73.6° (c 0.55, CH$_3$OH), solid oil, IR (KBr) v: 446, 503, 521, 557, 588, 621, 669, 700, 739, 774, 806, 847, 868, 910, 961, 974, 1007, 1057, 1096, 1111, 1169, 1262, 1285, 1310, 1366, 1406, 1454, 1476, 1522, 1584, 1653, 1692, 2720, 2834, 2878, 2934, 2976, 3030, 3065, 3088, 3104, 3300, 3491 cm$^{-1}$; $^1$H NMR (CDCl$_3$) δ: 8.41 7.32–6.98 (m, 8H, 2Ph), 4.77 (m, 1H, PheCH$^α$), 3.77–3.40 (m, 2H), 3.34 (s, 3H, OMe), 3.30–3.08 (m, 4H), 2.40–2.34 (m, 1H), 1.80–1.50 (m, 6H), 1.43 (s, 9H, t-Bu), 1.1 (d, 3H, J 5.5 Hz, Me); EIMS (70 eV) m/z (%): 578 (M$^+$, 0.17).

EXAMPLE II-i
Synthesis of N-tert-Butoxycarbonyl-(S,R,R)-Dolaproinyl-L-Methionine N-1-(2-p-Chlorophenylethyl) Amide (6i)

Reaction of N-tert-Boc-dolaproine (5) with the methionine amide hydrochloride (4i) according to General Procedure I, gave the Boc-dipeptide amide (6i) (C$_{27}$H$_{42}$N$_3$O$_5$S$_1$Cl$_1$, 72%), Rf=0.19 (hexane-acetone 3:1), m.p. 146°–148° C., [α]$_D$$^{23}$=−44.0° (c 0.15, CHCl$_3$), IR (KBr) v: 469, 519, 544, 594, 669, 712, 745, 775, 808, 837, 866, 918, 974, 1017, 1063, 1094, 1109, 1169, 1211, 1233, 1252, 1271, 1310, 1339, 1366, 1397, 1456, 1493, 1543, 1634, 1694, 1761, 1844, 1869, 1892, 2363, 2832, 2876, 2932, 2974, 3032, 3104, 3277 cm$^{-1}$, $^1$H NMR (CDCl$_3$) δ: 7.068–7.260 (m, 4H, ArH), 6.997, 6.692–6.714 (m, 1H, Ar—NH), 6.410, 6.299–6.316 (m, 1H, NH), 4.455–4.549 (m, 1H, H$^α$), 3.647–3.796 (m, 2H, N—CH, CH—OCH$_3$), 3.401 (s, 3H, OCH$_3$), 3.164–3.560 (m, 4H, N—CH$_2$, NH—CH$_2$), 2.7–2.8 (m, 2H, Ar—CH$_2$), 2.5–2.6 (m, 2H, CH$_2$$^γ$), 2.4–2.5 (m, 1H, CH—CH$_3$), 1.65–2.2 (m, 6H, CH$_2$$^β$, CH$_2$—CH$_2$), 2.070 (s, 3H, CH$_3$$^ε$), 1.429 (s, 9H, t-Bu), 1.22 (m, 3H, CH$_3$); EIMS (70 eV) m/z (%): 555 (M$^+$, 1).

EXAMPLE II-j
Synthesis of N-tert-Butoxycarbonyl-(S,R,R)-Dolaproinyl-L-Phenylalanine N-2-(6-Fluoro)benzothiazole Amide (6j)

Reaction of N-tert-Boc-dolaproine (5) with the phenylalanine amide hydrochloride (4j) followed by chromatography (hexane-acetone 3:1) according to General Procedure H, gave the Boc-dipeptide amide (6j) (C$_{30}$H$_{37}$N$_4$O$_5$S$_1$F$_1$, 95%), Rf=0.27 (hexane-acetone 3:1), [α]$_D$$^{25}$=−23.2° (c 0.57, CH$_3$OH), M.p. 110°–112° C., IR (KBr) v: 436, 475, 509, 540, 552, 569, 592, 627, 652, 669, 700, 746, 774, 812, 824, 853, 895, 912, 928, 953, 974, 990, 1032, 1049, 1065, 1107, 1171, 1217, 1250, 1263, 1283, 1302, 1317, 1339, 1366, 1395, 1458, 1478, 1499, 1561, 1611, 1643, 1697, 2743, 2878, 2938, 2972, 3084, 3160, 3190, 3256, 3335 cm$^{-1}$; $^1$H NMR (CDCl$_3$) δ: 7.65–7.07 (m, 8H, 2Ph), 4.88 (m, 1H, PheCH$^α$), 3.84–3.43 (m, 2H), 3.36 (s, 3H, OMe), 3.31–3.00 (m, 4H), 2.42–2.36 (m, 1H), 1.80–1.50 (m, 6H), 1.43 (s, 9H, t-Bu), 1.11 (d, 3H, J 6.1 Hz, Me); EIMS (70 eV) m/z 584 (M$^+$, 0.61).

EXAMPLE II-k
Synthesis of N-tert-Butoxycarbonyl-(S,R,R)-Dolaproinyl-L-Phenylalanine N-2-(6-Chloro)benzothiazole Amide (6k)

Reaction of N-tert-Boc-dolaproine (5) with the phenylalanine amide hydrochloride (4k) followed by chromatography (hexane-acetone 3:1) according to General Procedure H, gave the Boc-dipeptide amide (6k) (C$_{30}$H$_{37}$N$_4$O$_5$S$_1$Cl$_1$, 91%), Rf=0.30 (hexane-acetone 3:1), [α]$_D$$^{25}$=−32.6° (c 0.72, CH$_3$OH), M.p. 93°–95° C., IR (KBr) v: 503, 540, 561, 592, 623, 662, 698, 745, 766, 814, 853, 864, 891, 916, 974, 991, 1032, 1099, 1169, 1262, 1287, 1310, 1366, 1398, 1445, 1478, 1499, 1549, 1599, 1649, 1694, 2876, 2934, 2976, 3065, 3138, 3183, 3339 cm$^{-1}$; $^1$H NMR (CDCl$_3$) d: 7.74–7.10 (m, 8H, 2Ph), 4.85 (m, 1H, PheCH$^α$), 3.83–3.42 (m, 2H), 3.36 (s, 3H, OMe), 3.28–3.00 (m, 4H), 2.42–2.36 (m, 1H), 1.80–1.50 (m, 6H), 1.44 (s, 9H, t-Bu), 1.10 (d, 3H, J 6.7 Hz, Me); EIMS (70 eV) m/z (%): 601 (M$^+$, 0.16).

EXAMPLE II-l
Synthesis of N-tert-Butoxycarbonyl-(S,R,R)-Dolaproinyl-L-(p-Chloro) phenylalanine N-2-(6-Chloro)benzothiazole Amide (6l)

Reaction of N-tert-Boc-dolaproine (5) with the (p-chloro) phenylalanine amide hydrochloride (4l) followed by chromatography (hexane-acetone 3:1) according to General Procedure H, gave the Boc-dipeptide amide (6l) (C$_{30}$H$_{36}$N$_4$O$_5$S$_1$Cl$_2$, 98%), Rf=0.28 (hexane-acetone 3:1), [α]$_D$$^{25}$=−11.1° (c 0.18, CH$_3$OH), M.p. 107°–109° C., IR (KBr) v: 527, 563, 619, 644, 665, 698, 729, 766, 789, 814, 864, 918, 978, 991, 1017, 1036, 1053, 1099, 1167, 1262, 1287, 1310, 1339, 1366, 1400, 1445, 1478, 1493, 1549, 1599, 1649, 1692, 1771, 2878, 2934, 2976, 3067, 3138, 3181, 3206, 3318 cm$^{-1}$; $^1$H NMR (CDCl$_3$) δ: 7.74–7.10 (m, 8H, 2Ph), 4.85 (m, 1H, PheCH$^\alpha$), 3.82–3.42 (m, 2H), 3.37 (s, 3H, OMe), 3.30–3.00 (m, 4H), 2.43–2.36 (m, 1H), 1.80–1.50 (m, 6H), 1.44 (s, 9H, t-Bu), 1.13 (d, 3H, J 7.2 Hz, Me); EIMS (70 eV) m/z (%): 634 (M$^+$, 0.95).

EXAMPLE II-m

Synthesis of N-tert-Butoxycarbonyl-(S,R,R)-Dolaproinyl-L-Methionine N-2-Benzothiazole Amide (6m)

Reaction of N-tert-Boc-dolaproine (5) with the methionine amide hydrochloride (4m) followed by chromatography (hexane-acetone 3:1) according to General Procedure J, gave the dipeptide amide (6m) (C$_{26}$H$_{38}$N$_4$O$_5$S$_2$, 56%), Rf=0.52 (hexane-acetone 3:2), [α]$_D$$^{25}$=−69° (c 0.32, CH$_3$OH), M.p. 183°–185° C., IR (KBr) v: 596, 687, 727, 754, 822, 866, 895, 926, 970, 1017, 1036, 1103, 1167, 1211, 1223, 1265, 1292, 1317, 1341, 1366, 1397, 1441, 1454, 1478, 1530, 1553, 1603, 1643, 1697, 2876, 2930, 2974, 3059, 3071, 3148, 3187, 3331 cm$^{-1}$; $^1$H NMR (CDCl$_3$) δ: 7.79–7.70 (m, 2H, Ar—H), 7.46–7.24 (m, 2H, Ar—H), 6.68 (bs, 1H, NH—Met), 4.84 (bs, 1H, NH-BnThz), 4.75–4.70 (m, 1H, H$^\alpha$—Met), 3.93–3.78 (m, 2H, H$^\alpha$-Pro, CH-Dap), 3.50–3.19 (m, 3H), 3.45 (s, 3H, OMe), 2.65–2.47 (m, 2H, CH—OMe, CH—Me), 2.32–1.65 (m, 6H, 3×CH$_2$), 2.10 (s, 3H, S—Me), 1.43 (2s, 9H, t-Bu), 1.29 (d, J 7.7 Hz, 3H, CH$_3$); EIMS m/z (%): 550 (M$^+$, 31).

EXAMPLE II-n

Synthesis of N-tert-Butoxycarbonyl-(S,R,R)-Dolaproinyl-L-Proline N-2-Benzothiazole Amide (6n)

Reaction of N-tert-Boc-dolaproine (5) with the proline amide hydrochloride (4n) followed by chromatography (hexane-acetone 3:1) according to General Procedure J, gave the dipeptide amide (6n) as a glassy solid (C$_{26}$H$_{36}$N$_4$O$_5$S, 78%), Rf=0.47 (hexane-acetone 3:2), [α]$_D$$^{25}$=−138.3° (c 0.18, CH$_3$OH), M.p. 94°–96° C., IR (KBr) v: 436, 480, 507, 523, 544, 565, 602, 669, 704, 729, 758, 820, 868, 891, 920, 978, 1017, 1036, 1099, 1167, 1262, 1317, 1366, 1398, 1443, 1456, 1549, 1603, 1624, 1651, 1694, 1844, 1869, 2336, 2363, 2834, 2878, 2934, 2974, 3065, 3142, 3190, 3360, 3378, 3420, 3447, 3482, 3567 cm$^{-1}$; $^1$H NMR (CDCl$_3$) δ: 7.80–7.76 (m, 2H, Ar—H), 7.43–7.24 (m, 2H, Ar—H), 4.88–4.81 (bs, 1H, NH-BnThz), 4.11–3.81 (m, H, H$^\alpha$-Pro, CH-Dap), 3.60–3.15 (m, 4H, 2×CH$_2$), 3.45 (s, 3H, OMe), 2.73–2.54 (m, 2H, CH—OMe, CH—Me), 2.18–1.65 (m, 8H, 4×CH$_2$), 1.50–1.44 (2s, 9H, t-Bu), 1.27 (d, J 7.2 Hz, 3H, CH$_3$); EIMS m/z (%): (M$^+$, 2).

EXAMPLE II-o

Synthesis of N-tert-Butoxycarbonyl-(S,R,R)-Dolaproinyl-L-Methionine N-2-Pyridyl Amide (6o)

Reaction of N-tert-Boc-dolaproine (5) with the methionine amide trifluoroacetate (4o) followed by chromatography (hexane-acetone 3:2) according to General Procedure H, gave the Boc-dipeptide amide (6o) (C$_{24}$H$_{38}$N$_4$O$_5$S$_1$, 73%), Rf=0.20 (hexane-acetone 3:1), m.p. 123°–125° C., [α]$_D$$^{23}$= −69.3° (c 0.15, CHCl$_3$), IR (KBr) v: 488, 521, 556, 615, 631, 677, 741, 777, 868, 918, 961, 974, 993, 1067, 1111, 1169, 1244, 1296, 1366, 1395, 1435, 1460, 1532, 1578, 1595, 1640, 1694, 1888, 1908, 1944, 2836, 2878, 2932, 2974, 3055, 3123, 3250, 3325 cm$^{-1}$, $^1$H NMR (CDCl$_3$) δ: 9.020, 8.696 (s, 1H, Ar—NH), 8.238–8.283 (m, 1H, ArH), 8.121 (d, J 8.1 Hz, 1H, ArH), 7.627–7.690 (m, 1H, ArH), 6.964–7.044, 6.531 (m, 1H, NH), 4.6–4.8 (m, 1H, H$^\alpha$), 3.7–4.0 (m, 2H, N—CH, CH—OCH$_3$), 3.431 (s, 3H, OCH$_3$), 3.2–3.6 (m, 2H, N—CH$_2$), 2.6–2.7 (m, 2H, CH$_2$$^\gamma$), 2.4–2.5 (m, 1H, CH—CH$_3$), 1.6–2.3 (m, 6H, CH$_2$$^\beta$, CH$_2$—CH$_2$), 2.110 (s, 3H, CH$_3$$^\epsilon$), 1.432, 1.412 (s, 9H, t-Bu), 1.264 (m, 3H, CH$_3$); EIMS (70 eV) m/z (%): 494 (M$^+$, 2).

EXAMPLE II-p

Synthesis of N-tert-Butoxycarbonyl-(S,R,R)-Dolaproinyl-L-Methionine N-3-Quinoline Amide (6p)

Reaction of N-tert-Boc-dolaproine (5) with the methionine amide hydrochloride (4p) followed by chromatography (hexane-acetone-ethyl acetate 5:4:1) according to General Procedure J, gave the dipeptide amide (6p) (C$_{28}$H$_{40}$N$_4$O$_5$S, 60%), Rf=0.34 (hexane-acetone 3:2), [α]D$^{25}$=−89.2° (c 0.13, CH$_3$OH), M.p. 228°–230° C., IR (KBr) v: 453, 476, 521, 548, 596, 615, 640, 669, 700, 731, 752, 785, 818, 864, 889, 918, 955, 976, 990, 1015, 1040, 1067, 1107, 1167, 1240, 1283, 1308, 1339, 1368, 1398, 1424, 1456, 1489, 1506, 1541, 1576, 1634, 1684, 1771, 1792, 2338, 2363, 2832, 2874, 2930, 2974, 3042, 3075, 3123, 3223, 3248, 3310 cm$^{-1}$; $^1$H NMR (CDCl$_3$) δ: 9.47, 4.34 (bs, 1H, NH-Quinoline), 8.79, 8.68 (2s, 2H, Ar—H), 8.01–7.25 (m, 4H, Ar—H), 6.66 (bs, 1H, NH—Met), 4.78–4.72 (m, 1H, H$^\alpha$—Met), 3.89–3.78 (m, 2H, H$^\alpha$-Dap, CH—OMe), 3.56–3.18 (m, 3H), 3.44 (s, 3H, OMe), 2.74–1.68 (m, 8H, 4×CH$_2$), 2.12 (s, 3H, S—Me), 1.46, 1.39 (2s, 9H, t-Bu), 1.30 (d, J 6.6 Hz, 3H, CH$_3$); EIMS m/z (%): 544 (M$^+$, 4).

EXAMPLE II-q

Synthesis of N-tert-Butoxycarbonyl-(S,R,R)-Dolaproinyl-L-Proline N-3-Quinoline Amide (6g)

Reaction of N-tert-Boc-dolaproine (5) with the proline amide hydrochloride (4g) followed by chromatography (hexane-acetone 3:2) according to General Procedure J, gave the dipeptide amide (6g) as glassy solid (C$_{28}$H$_{38}$N$_4$O$_5$, 60%), Rf=0.21 (hexane-acetone 3:2), [α]$_D$$^{25}$=−163.1° (c 0.16, CH$_3$OH), M.p. 92°–94° C., IR (KBr) v: 475, 544, 565, 598, 615, 669, 691, 748, 781, 820, 866, 901, 953, 970, 988, 1017, 1059, 1099, 1167, 1192, 1221, 1242, 1283, 1366, 1395, 1439, 1456, 1491, 1522, 1559, 1580, 1618, 1653, 1696, 1771, 1792, 1829, 1844, 1867, 1877, 1890, 1917, 1942, 1960, 2338, 2361, 2834, 2878, 2934, 2974, 3061, 3098, 3169, 3194, 3250, 3289, 3397, 3424, 3447, 3462, 3482, 3567 cm$^{-1}$; $^1$H NMR (CDCl$_3$) δ: 10.33 (bs, 1H, NH-Quinoline), 8.78, 8.50 (m, 2H, Ar—H), 8.02–7.43 (m, 4H, Ar—H), 4.90 (m, 1H, H$^\alpha$-Pro), 4.07–3.86 (m, 2H, H$^\alpha$-Dap, CH—OMe), 3.62–2.56 (m, 5H), 3.47 (s, 3H, OMe), 2.18–1.56 (m, 8H, 4×CH$_2$), 1.51–1.44 (2s, 9H, t-Bu), 1.28 (d, J 7.2 Hz, 3H, CH$_3$); EIMS m/z (%): 510 (M$^+$, 3).

EXAMPLE II-r

Synthesis of N-tert-Butoxycarbonyl-(S,R,R)-Dolaproinyl-L-Valine N-3-Quinoline Amide (6r)

Reaction of N-tert-Boc-dolaproine (5) with the valine amide hydrochloride (4r) followed by chromatography (hexane-acetone 3:1) according to General Procedure J, gave the dipeptide amide (6r) (C$_{28}$H$_{40}$N$_4$O$_5$, 62%), Rf=0.38 (hexane-acetone 3:2), [α]$_D$$^{25}$=−108.0° (c 0.25, CH$_3$OH), M.p. 209.2°–210.3° C., IR (KBr) v: 449, 478, 581, 613, 644, 679, 706, 718, 754, 785, 856, 899, 924, 939, 959, 974, 991, 1007, 1018, 1063, 1092, 1113, 1144, 1169, 1219, 1265, 1277, 1321, 1368, 1391, 1466, 1491, 1555, 1578, 1643, 1678, 1697, 2832, 2876, 2893, 2934, 2967, 3061, 3127, 3264, 3306 cm$^{-1}$; $^1$H NMR (CDCl$_3$) δ: 9.35, 9.23 (2bs, 1H, NH-Quinoline), 8.79, 8.69 (2bs, 1H, Ar—H), 8.76, 8.65 (2s, 1H, Ar—H), 7.98–7.42 (m, 4H, Ar—H), 6.95, 6.55 (2bd, J 7.2 Hz, 1H, NH-Val), 4.45–4.40 (m, 1H, H$^\alpha$-Val), 3.91–3.81 (m, 2H, H$^\alpha$-Dap, CH-Ome), 3.88–3.25 (m, 2H, CH$_2$$^\delta$-Pro), 3.45 (s, 3H, Ome), 2.56–1.69 (m, 8H), 1.45, 1.38 (2s, 9H, t-Bu), 1.30 (d, J 6.6 Hz, 3H, CH$_3$), 1.06 (d, J 6.7 Hz, 6H, Me$^{\gamma,\gamma}$-Val); EIMS m/z (%): 512 (M$^+$, 4).

EXAMPLE II-s
Synthesis of N-tert-Butoxycarbonyl-(S,R,R)-Dolaproinyl-L-Isoleucine N-3-Quinoline Amide (6s)

Reaction of N-tert-Boc-dolaproine (5) with the isoleucine amide hydrochloride (4s) followed by chromatography (hexane-acetone 3:2) according to General Procedure J, gave the dipeptide amide (6s) ($C_{29}H_{42}N_4O_5$, 59%), Rf=0.43 (hexane-acetone 3:2), $[\alpha]_D^{25}$=−97.0° (c 0.1, $CH_3OH$), M.p. 198.0°–198.7° C., IR (KBr) ν: 478, 523, 548, 579, 613, 702, 758, 770, 785, 862, 899, 918, 934, 959, 974, 991, 1042, 1065, 1094, 1111, 1144, 1167, 1217, 1256, 1279, 1368, 1391, 1458, 1491, 1543, 1576, 1642, 1680, 1697, 1792, 1844, 1869, 1890, 1906, 1919, 1942, 2338, 2363, 2832, 2880, 2934, 2974, 3067, 3127, 3264, 3306 cm$^{-1}$; $^1$H NMR ($CDCl_3$) δ: 9.27, 9.03 (2bs, 1H, NH-Quinoline), 8.82, 8.63 (2bs, 1H, Ar—H), 8.73 (s, 1H, Ar—H), 7.99–7.44 (m, 4H, Ar—H), 6.96, 6.50 (2d, J 7.8 Hz, 1H, NH-Ile), 4.48–4.43 (m, 1H, H$^\alpha$-Ile), 3.91–3.78 (m, 2H, H$^\alpha$-Dap, CH—OMe), 3.56–3.21 (m, 2H, $CH_2^\delta$-Pro), 3.45 (s, 3H, OMe), 2.55–2.45 (m, 1H, CH—Me), 2.22–1.33 (m, 7H), 1.45, 1.39 (2s, 9H, t-Bu), 1.30 (d, J 6.7 Hz, 3H, $CH_3$), 1.04 (d, J 6.7 Hz, 3H, Me$^\beta$-Ile), 0.75 (t, J 7.8 Hz, 3H, Me$^\delta$-Ile); EIMS m/z (%): 526 (M$^+$, 4).

EXAMPLE III
The synthesis of pentapeptide amides (9a–s) proceeded following General Procedure L, as shown below.

EXAMPLE III-a
Synthesis of L-Dolavalyl-L-Valyl-N-Methyl-(S,S,R)-Dolaisoleuinyl-(S,R,R)-Dolaproinyl-L-Methionine N-4-Fluorophenyl Amide (9a)

Chromatography over a SILICA GEL column with hexane-acetone (1:1) as eluent, according to General Procedure L, gave 9a as a white solid ($C_{42}H_{71}N_6O_7S_1F_1$, 88%), Rf=0.32 (hexane-acetone 1:1), M.p. 95°–100° C., $[\alpha]_D^{23}$=−47.2°(c 0.25, $CHCl_3$), IR (KBr) ν: 517, 546, 586, 610, 629, 683, 719, 775, 814, 835, 961, 976, 1038, 1099, 1159, 1213, 1254, 1304, 1341, 1371, 1387, 1412, 1449, 1510, 1549, 1624, 1649, 2789, 2832, 2876, 2936, 2967, 3067, 3160, 3295 cm$^{-1}$; EIMS (70 eV) m/z (%): 823 (M$^+$, 2).

EXAMPLE III-b
Synthesis of L-Dolavalyl-L-Valyl-N-Methyl-(S,S,R)-Dolaisoleuinyl-(S,R,R)-Dolaproinyl-L-Methionine N-2-Chlorophenyl Amide (9b)

Chromatography over a SILICA GEL with hexane-acetone (1:2) as eluent, according to General Procedure L, yielded 9b as a white solid ($C_{42}H_{71}N_6O_7S_1Cl_1$, 89%), Rf=0.33 (hexane-acetone 1:1), M.p. 95°–100° C., $[\alpha]_D^{23}$=−67.1° (c 0.17, $CHCl_3$), IR (KBr) ν: 550, 561, 611, 631, 691, 719, 752, 837, 860, 961, 976, 1036, 1057, 1099, 1132, 1200, 1244, 1294, 1341, 1385, 1418, 1441, 1532, 1595, 1624, 1643, 1869, 1879, 1888, 1902, 1919, 1929, 1946, 1956, 2787, 2832, 2876, 2934, 2965, 3034, 3111, 3123, 3298, 3389, 3470 cm$^{-1}$; EIMS (70 eV) m/z (%): 838 (M$^+$, 4).

EXAMPLE III-c
Synthesis of L-Dolavalyl-L-Valyl-N-Methyl-(S,S,R)-Dolaisoleuinyl-(S,R,R)-Dolaproinyl-L-Methionine N-3-Chlorophenyl Amide (9c)

Chromatography over a SILICA GEL with hexane-acetone (1:1) as eluent, according to General Procedure L, yielded 9c ($C_{42}H_{71}N_6O_7S_1Cl_1$, 88%), Rf=0.35 (hexane-acetone 1:1), M.p. 105°–110° C., $[\alpha]_D^{23}$=−49.4° (c 0.16, $CHCl_3$), IR (KBr) ν: 613, 631, 683, 719, 777, 880, 961, 974, 999, 1009, 1038, 1099, 1132, 1202, 1252, 1267, 1310, 1370, 1387, 1425, 1449, 1483, 1541, 1595, 1624, 1651, 2787, 2832, 2876, 2934, 2967, 3061, 3127, 3295 cm$^{-1}$; EIMS (70 eV) m/z (%): 838 (M$^+$, 0.88).

EXAMPLE III-d
Synthesis of L-Dolavalyl-L-Valyl-N-Methyl-(S,S,R)-Dolaisoleuinyl-(S,R,R)-Dolaproinyl-L-Phenylalanine N-3-Chlorophenyl Amide (9d)

Chromatography over a SILICA GEL with hexane-acetone (1:1) as eluent, according to General Procedure L, yielded 9d ($C_{46}H_{71}N_6O_7Cl_1$, 77%), Rf=0.41 (hexane-acetone 1:1), M.p. 115°–120° C., $[\alpha]_D^{23}$=−62.8° (c 0.18, $CHCl_3$), IR (KBr) ν: 500, 565, 584, 611, 629, 683, 698, 743, 777, 880, 974, 999, 1038, 1099, 1167, 1192, 1250, 1267, 1287, 1306, 1339, 1370, 1387, 1425, 1454, 1483, 1541, 1595, 1624, 1649, 2832, 2876, 2936, 2967, 3030, 3063, 3198, 3300 cm$^{-1}$; EIMS (70 eV) m/z (%): 854 (M$^+$).

EXAMPLE III-e
Synthesis of L-Dolavalyl-L-Valyl-N-Methyl-(S,S,R)-Dolaisoleuinyl-(S,R,R)-Dolaproinyl-L-Methionine N-4-Chlorophenyl Amide (9e)

Chromatography over a SILICA GEL with hexane-acetone (1:1) as eluent, according to General Procedure L, yielded 9e as a glassy solid ($C_{42}H_{71}N_6O_7S_1Cl_1$, 79%), Rf=0.35 (hexane-acetone 1:1), M.p. 100°–110° C., $[\alpha]D_D^{23}$=−53.5° (c 0.27, $CHCl_3$), IR (KBr) ν: 511, 563, 610, 631, 681, 719, 775, 801, 831, 893, 907, 961, 976, 1013, 1038, 1096, 1132, 1179, 1202, 1248, 1289, 1310, 1341, 1404, 1416, 1451, 1493, 1541, 1649, 1873, 1888, 1917, 1937, 1952, 1973, 2660, 2672, 2789, 2832, 2878, 2936, 2967, 3059, 3123, 3200, 3291 cm$^{-1}$; EIMS (70 eV) m/z (%): 838 (M$^+$, 0.40).

EXAMPLE III-f
Synthesis of L-Dolavalyl-L-Valyl-N-Methyl-(S,S,R)-Dolaisoleuinyl-(S,R,R)-Dolaproinyl-L-Phenylalanine N-4-Chlorophenyl Amide (9f)

Chromatography over a SILICA GEL with hexane-acetone (1:1) as eluent, according to General Procedure L, yielded 9f ($C_{46}H_{71}N_6O_7Cl_1$, 93%), Rf=0.38 (hexane-acetone 1:1); $[\alpha]_D^{25}$=−58.7° (c 0.23, $CH_3OH$). M.p. 105°–110° C., IR (KBr) ν: 503, 563, 610, 629, 677, 700, 743, 775, 828, 974, 1013, 1038, 1096, 1175, 1194, 1248, 1267, 1289, 1306, 1370, 1387, 1404, 1416, 1454, 1493, 1541, 1624, 1649, 2787, 2832, 2876, 2934, 2965, 3030, 3063, 3123, 3198, 3306 cm$^{-1}$; EIMS (70 eV) m/z (%): 855 (M$^+$, 1).

EXAMPLE III-g
Synthesis of L-Dolavalyl-L-Valyl-N-Methyl-(S,S,R)-Dolaisoleuinyl-(S,R,R)-Dolaproinyl-L-Methionine N-2,5-Dichlorophenyl Amide (9g)

Chromatography over a SILICA GEL with hexane-acetone (2:3) as eluent, according to General Procedure L, yielded 9g ($C_{42}H_{71}N_6O_7S_1Cl_1$, 87%),Rf=0.41 (hexane-acetone 1:1), M.p. 110°–120° C., $[\alpha]_D^{23}$=−64.2° (c 0.24, $CHCl_3$), IR (KBr) ν: 527, 561, 586, 610, 633, 681, 719, 802, 828, 978, 1038, 1096, 1132, 1175, 1200, 1262, 1304, 1412, 1452, 1526, 1584, 1624, 1645, 1659, 1798, 2787, 2832, 2878, 2936, 2967, 3104, 3117, 3297 cm$^{-1}$; EIMS (70 eV) m/z (%): 872 (M$^+$, 0.85).

EXAMPLE III-h
Synthesis of L-Dolavalyl-L-Valyl-N-Methyl-(S,S,R)-Dolaisoleuinyl-(S,R,R)-Dolaproinyl-L-Phenylalanine N-2,5-Dichlorophenyl Amide (9h)

Chromatography over a SILICA GEL with hexane-acetone (1:1) as eluent, according to General Procedure L, yielded 9h ($C_{46}H_{70}N_6O_7Cl_2$, 46%), Rf=0.46 (hexane-acetone 1:1); $[\alpha]_D^{23}$=−81.5° (c 0.20, $CH_3OH$), M.p. 102°–105° C., IR (KBr) ν: 448, 503, 530, 557, 588, 629, 667, 700, 748, 775, 812, 849, 860, 880, 914, 976, 1017, 1040, 1053, 1094, 1134, 1167, 1262, 1285, 1370, 1410, 1454, 1524, 1584, 1622, 1688, 1705, 1842, 2363, 2787, 2832, 2876, 2934, 2969, 3030, 3063, 3298 cm$^{-1}$; EIMS (70 eV) m/z (%): 889 (M$^+$, 2).

EXAMPLE III-i

Synthesis of L-Dolavalyl-L-Valyl-N-Methyl-(S,S,R)-Dolaisoleuinyl-(S,R,R)-Dolaproinyl-L-Methionine N-1-(2-p-Chlorophenylethyl) Amide (9i)

Chromatography over a SILICA GEL with hexane-acetone (1:2) as eluent, according to General Procedure L, yielded 9i ($C_{44}H_{74}N_6O_7S_1Cl_1$, 77%), Rf=0.26 (hexane-acetone 1:1), M.p. 117°–120° C., $[\alpha]_D^{23}$=–60.0° (c 0.10, CHCl$_3$), IR (KBr) ν: 505, 523, 544, 567, 610, 627, 679, 719, 777, 801, 816, 831, 961, 974, 1015, 1038, 1096, 1134, 1200, 1248, 1267, 1285, 1306, 1387, 1418, 1445, 1493, 1539, 1628, 1647, 2789, 2832, 2878, 2934, 2967, 3061, 3293 cm$^{-1}$; EIMS (70 eV) m/z (%): 866 (M$^+$, 1).

EXAMPLE III-j

Synthesis of L-Dolavalyl-L-Valyl-N-Methyl-(S,S,R)-Dolaisoleuinyl-(S,R,R)-Dolaproinyl-L-Phenylalanine N-2-(6-Fluoro)benzothiazole Amide (9j)

Chromatography over a SILICA GEL with hexane-acetone (1:1) as eluent, according to General Procedure L, yielded 9j ($C_{47}H_{70}N_7O_7S_1F_1$, 58%), Rf=0.32 (hexane-acetone 1:1); $[\alpha]_D^=$=–40.8° (c 0.26, CH$_3$OH), M.p. 123°–125° C., IR (KBr) ν: 438, 475, 502, 540, 579, 610, 631, 664, 700, 745, 775, 826, 851, 880, 893, 912, 963, 974, 986, 1036, 1051, 1099, 1167, 1198, 1225, 1252, 1285, 1317, 1341, 1370, 1387, 1416, 1458, 1499, 1557, 1622, 1699, 2787, 2830, 2876, 2936, 2967, 3067, 3198, 3297 cm$^{-1}$; EIMS (70 eV) m/z (%): 895 (M$^+$, 3).

EXAMPLE III-k

Synthesis of L-Dolavalyl-L-Valyl-N-Methyl-(S,S,R)-Dolaisoleuinyl-(S,R,R)-Dolaproinyl-L-Phenylalanine N-2-(6-Chloro)benzothiazole Amide (9k)

Chromatography over a SILICA GEL with hexane-acetone (1:1) as eluent, according to General Procedure L, yielded 9k ($C_{47}H_{70}N_7O_7S_1Cl_1$, 83%), Rf=0.35 (hexane-acetone 1:1); $[\alpha]_D^{25}$=–43.6° (c 0.25, CH$_3$OH), M.p. 127°–129° C., IR (KBr) ν: 424, 434, 498, 534, 563, 623, 662, 698, 746, 766, 814, 853, 880, 891, 910, 961, 988, 1038, 1053, 1099, 1169, 1190, 1223, 1260, 1287, 1310, 1370, 1387, 1418, 1445, 1499, 1549, 1599, 1622, 1701, 2787, 2830, 2876, 2934, 2967, 3028, 3063, 3135, 3181, 3204, 3297 cm$^{-1}$; EIMS (70 eV) m/z (%): 912 (M$^+$, 0.60).

EXAMPLE III-l

Synthesis of L-Dolavalyl-L-Valyl-N-Methyl-(S,S,R)-Dolaisoleuinyl-(S,R,R)-Dolaproinyl-L-(p-Chloro)phenylalanine N-2-(6-Chloro)benzothiazole Amide (9l)

Chromatography over a SILICA GEL with hexane-acetone (1:1) as eluent, according to General Procedure L, yielded 9l ($C_{47}H_{69}N_7O_7S_1Cl_2$, 56%), Rf=0.37 (hexane-acetone 1:1); $[\alpha]_D^{25}$=–30.0° (c 0.22, CH$_3$OH), M.p. 132°–135° C., IR (KBr) ν: 525, 563, 610, 621, 633, 642, 669, 698, 766, 814, 855, 880, 909, 930, 959, 988, 1017, 1038, 1053, 1098, 1171, 1182, 1192, 1223, 1262, 1287, 1310, 1339, 1370, 1387, 1416, 1445, 1495, 1549, 1599, 1624, 1638, 1701, 2666, 2787, 2830, 2876, 2934, 2967, 3063, 3136, 3208, 3295 cm$^{-1}$; EIMS (70 eV) m/z (%): 945 (M$^+$, 0.05).

EXAMPLE III-m

Synthesis of L-Dolavalyl-L-Valyl-N-Methyl-(S,S,R)-Dolaisoleuinyl-(S,R,R)-Dolaproinyl-L-Methionine N-2-Benzothiazole Amide (9m)

Chromatography over a SILICA GEL with acetone-hexane (3:2) as eluent, according to General Procedure L, yielded 9m ($C_{43}H_{71}N_7O_7S_2$, 87%), Rf=0.47 (hexane-acetone 2:3), $[\alpha]_D^{25}$=–45° (c 0.14, CH$_3$OH), M.p. 118°–120° C., IR (KBr) ν: 548, 561, 610, 629, 687, 729, 758, 801, 816, 829, 868, 880, 959, 976, 1017, 1038, 1098, 1132, 1200, 1225, 1263, 1308, 1316, 1370, 1385, 1418, 1443, 1547, 1622, 1647, 2789, 2832, 2876, 2934, 2969, 3061, 3194, 3212, 3287 cm$^{-1}$; EIMS m/z (%): 862 (M$^+$).

EXAMPLE III-n

Synthesis of L-Dolavalyl-L-Valyl-N-Methyl-(S,S,R)-Dolaisoleuinyl-(S,R,R)-Dolaproinyl-L-Proline N-2-Benzothiazole Amide (9n)

Chromatography over a SILICA GEL with chloroform-methanol (7:1) as eluent, according to General Procedure L, yielded 9n ($C_{43}H_{69}N_7O_7S$, 80%), Rf=0.23 (hexane-acetone 2:3), $[\alpha]_D^{25}$=–100.0° (c 0.22, CH$_3$OH), M.p. 199°–200° C., IR (KBr) ν: 434, 559, 604, 615, 642, 679, 704, 729, 756, 810, 835, 855, 868, 893, 918, 951, 966, 980, 1017, 1040, 1053, 1098, 1140, 1161, 1192, 1235, 1262, 1290, 1316, 1370, 1385, 1420, 1445, 1489, 1549, 1638, 1696, 2787, 2830, 2876, 2932, 2961, 3065, 3129, 3169, 3322 cm$^{-1}$; EIMS m/z (%): 828 (M$^+$, 24).

EXAMPLE III-o

Synthesis of L-Dolavalyl-L-Valyl-N-Methyl-(S,S,R)-Dolaisoleuinyl-(S,R,R)-Dolaproinyl-L-Methionine N-2-Pyridyl Amide (9o)

Chromatography over a SILICA GEL with hexane-acetone (1:1) as eluent, according to General Procedure L, yielded 9o ($C_{41}H_{71}N_7O_7S_1$, 77%), Rf=0.22 (hexane-acetone 1:1), M.p. 100°–110° C., $[\alpha]_D^{23}$=–56.9° (c 0.16, CHCl$_3$), IR (KBr) ν: 525, 559, 615, 685, 719, 741, 781, 833, 976, 991, 1009, 1038, 1098, 1132, 1152, 1200, 1246, 1298, 1343, 1371, 1385, 1435, 1460, 1534, 1578, 1626, 2789, 2832, 2876, 2934, 2967, 3044, 3113, 3291, 3408 cm$^{-1}$; EIMS (70 eV) m/z (%): 806 (M$^+$, 2).

EXAMPLE III-p

Synthesis of L-Dolavalyl-L-Valyl-N-Methyl-(S,S,R)-Dolaisoleuinyl-(S,R,R)-Dolaproinyl-L-Methionine N-3-Quinoline Amide (9p)

Chromatography over a SILICA GEL with chloroform-methanol (7:1) as eluent, according to General Procedure L, yielded 9p as a glassy solid ($C_{43}H_{73}N_7O_7S$, 95%), Rf=0.41 (hexane-acetone 2:3), $[\alpha]_D^{25}$=–58.2° (c 0.11, CHCl$_3$), M.p. 98–100, IR (KBr) ν: 476, 503, 542, 567, 611, 633, 669, 683, 719, 754, 772, 785, 816, 831, 860, 880, 903, 959, 980, 990, 1009, 1038, 1099, 1136, 1159, 1196, 1221, 1285, 1306, 1346, 1370, 1420, 1456, 1491, 1557, 1578, 1624, 1653, 1771, 1792, 2338, 2363, 2473, 2527, 2596, 2660, 2689, 2741, 2789, 2832, 2876, 2936, 2967, 3057, 3291 cm$^{-1}$; EIMS m/z (%): 856 (M$^+$, 10).

EXAMPLE III-q

Synthesis of L-Dolavalyl-L-Valyl-N-Methyl-(S,S,R)-Dolaisoleuinyl-(S,R,R)-Dolaproinyl-L-Proline N-3-Quinoline Amide (9q)

Chromatography over a SILICA GEL with chloroform-methanol (7:1) as eluent, according to General Procedure L, yielded 9q ($C_{45}H_{71}N_7O_7$, 82%), Rf=0.11 (hexane-acetone 2:3), $[\alpha]_D^{25}$=–108.2° (c 0.11, CH$_3$OH), M.p. 149°–151° C., IR (KBr) ν: 476, 509, 527, 565, 613, 667, 691, 719, 754, 772, 903, 990, 1009, 1098, 1134, 1177, 1196, 1242, 1258, 1287, 1343, 1364, 1387, 1420, 1437, 1458, 1489, 1506, 1559, 1576, 1636, 1674, 1697, 1734, 2338, 2363, 2471, 2513, 2531, 2650, 2660, 2724, 2739, 2832, 2878, 2967, 3030, 3268, 3430, 3443, 3588 cm$^{-1}$; EIMS m/z (%): 822 (M$^+$, 36).

EXAMPLE III-r

Synthesis of L-Dolavalyl-L-Valyl-N-Methyl-(S,S,R)-Dolaisoleuinyl-(S,R,R)-Dolaproinyl-L-Valine N-3-Quinoline Amide (9r)

Chromatography over a SILICA GEL column with toluene-ethyl acetate-methanol (5:3:2) as eluent, according to General Procedure L, gave 9r as a white solid ($C_{45}H_{73}N_7O_7$, 86%), Rf=0.28 (hexane-acetone 2:3), $[\alpha]_D^{25}$=−78.7° (c 0.15, $CH_3OH$), M.p. 140°–142° C., IR (KBr) v: 476, 546, 561, 611, 629, 679, 719, 752, 783, 799, 837, 858, 901, 959, 990, 1038, 1099, 1134, 1200, 1219, 1263, 1346, 1370, 1387, 1420, 1466, 1491, 1555, 1580, 1626, 1649, 2789, 2832, 2876, 2936, 2965, 3057, 3289 $cm^{-1}$; EIMS m/z (%): 824 ($M^+$, 23).

EXAMPLE III-s

Synthesis of L-Dolavalyl-L-Valyl-N-Methyl-(S,S,R)-Dolaisoleuinyl-(S,R,R)-Dolaproinyl-L-Isoleucine N-3-Quinoline Amide (9s)

Chromatography over a SILICA GEL with toluene-ethyl acetate-methanol (5:3:2) as eluent, according to General Procedure L, yielded 9s as a white solid ($C_{46}H_{75}N_7O_7$, 81%), Rf=0.34 (hexane-acetone 2:3), $[\alpha]_D^{25}$=−70.9° (c 0.11, $CH_3OH$), M.p. 133°–135° C., IR (KBr) v: 476, 538, 611, 629, 669, 683, 719, 752, 783, 801, 837, 901, 980, 1036, 1099, 1134, 1169, 1200, 1217, 1262, 1346, 1370, 1385, 1420, 1458, 1491, 1506, 1541, 1559, 1578, 1624, 1653, 1734, 1771, 1792, 2361, 2789, 2832, 2878, 2936, 2967, 3057, 3133, 3291, 3567, 3588 $cm^{-1}$; EIMS m/z (%): 838 ($M^+$, 44).

Thus the synthesis of several heterocyclic and halophenyl amide derivatives of dolastatin 10 has been shown. These amide derivatives are more easily synthesized than dolastatin 10 and, like dolastatin 10, exhibit effective antineoplastic activity against various human tumor and mouse cell lines thereby rendering these derivatives as possible alternatives to dolastatin 10.

From the foregoing, it is readily apparent that a useful embodiment of the present invention has been herein described and illustrated which fulfills all of the aforestated objectives in a remarkably unexpected fashion. It is, of course, understood that such modifications, alterations and adaptations as may readily occur to the artisan confronted with this disclosure are intended within the spirit of this disclosure which is limited only by the scope of the claims appended hereto.

Accordingly, what is claimed is:

1. A composition having the general structure set forth below:

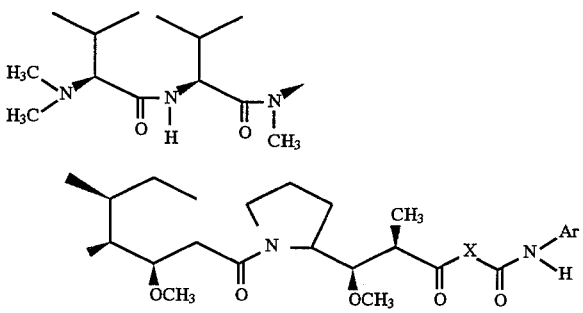

wherein substituents X and Ar are as set forth below:
   a) X=Met, Ar=4FPh;
   b) X=Met, Ar=2ClPh;
   c) X=Met, Ar=3ClPh;
   e) X=Met, Ar=4ClPh;
   g) X=Met, Ar=2,5diClPh;
   i) X=Met, Ar=4ClPEA;
   m) X=Met, Ar=BnThz;
   n) X=Pro, Ar=BnThz;
   o) X=Met, Ar=2Py;
   p) X=Met, Ar=3Q;
   q) X=Pro, Ar=3Q;
   r) X=Val, Ar=3Q; and
   s) X=Ile, Ar=3Q.

2. A composition of matter, denominated herein as 9(a), according to claim 1 wherein X=Met and Ar=4FPh.

3. A composition of matter, denominated herein as 9(b), according to claim 1 wherein X=Met and Ar=2ClPh.

4. A composition of matter, denominated herein as 9(c), according to claim 1 wherein X=Met and Ar=3ClPh.

5. A composition of matter, denominated herein as 9(e), according to claim 1 wherein X=Met and Ar=4ClPh.

6. A composition of matter, denominated herein as 9 (g), according to claim 1 wherein X=Met and Ar=2,5diClPh.

7. A composition of matter, denominated herein as 9(i), according to claim 1 wherein X=Met and Ar=4ClPEA.

8. A composition of matter, denominated herein as 9 (m), according to claim 1 wherein X=Met and Ar=BnThz.

9. A composition of matter, denominated herein as 9(n), according to claim 1 wherein X=Pro and Ar=BnThz.

10. A composition of matter, denominated herein as 9(o), according to claim 1 wherein X=Met and Ar=2Py.

11. A composition of matter, denominated herein as 9(p), according to claim 1 wherein X=Met and Ar=3Q.

12. A composition of matter, denominated herein as 9(q), according to claim 1 wherein X=Pro and Ar=3Q.

13. A composition of matter, denominated herein as 9(r), according to claim 1 wherein X=Val and Ar=3Q.

14. A composition of matter, denominated herein as 9 (s), according to claim 1 wherein X=Ile and Ar=3Q.

15. A method of synthesizing the compositions of claim 1 which comprises:
   (a) reacting an amine selected from the group consisting of: 4-fluoroaniline (2a); 2-chloroaniline (2b); 3-chloroaniline (2c); 4-chloroaniline (2d); 2,5-dichloroaniline (2e); 4-chlorophenethylamine (2f); 2-amino-6-fluorobenzothiazole (2g); 2-amino-6-chlorobenzothiazole (2h); 2-aminobenzothiazole (2i); 2-aminopyridine (2j); and 3-aminoquinoline (2k) with a Boc-L-amino acid selected from the group consisting of: N-tert-Boc-Methionine (1a); N-tert-Boc-Proline (1c); N-tert-Boc-Valine (1d); and N-tert-Boc-Isoleucine (1e); in the presence of a condensing agent selected from the group consisting of: 2-ethoxy-1-ethoxycarbonyl-1,2-dihydroquinoline (EEDQ); isobutylchloroformate; and 1,3-dicyclohexylcarbodiimide to form an amide;
   (b) removing the protecting group from said amide with a reagent selected from the group consisting of: hydrogen chloride in acetic acid; hydrogen chloride in dioxane; and trifluoroacetic acid in methylene chloride, to afford the corresponding hydrochloride/trifluoroacetate salt;
   (c) coupling said deprotected N-tert-butyloxycarbonyl-L-amino acid amide with dolaproine in the presence of diethylphosphorocyanidate and triethylamine to form a protected dipeptide amide;
   (d) removing the protecting group of the protected dipeptide amide with trifluoroacetic acid to form a corresponding trifluoroacetate salt; and
   (e) coupling each of said trifluoroacetate salts with tripeptide trifluoroacetate (TFA* Dov-Val-Dil-OH) in the presence of diethylphosphorocyanidate to form said synthetic composition.

16. A composition having the general structure set forth below:

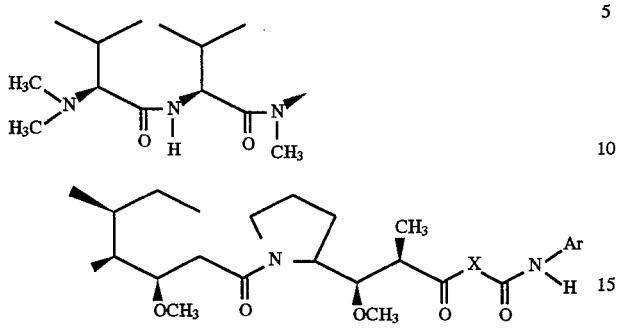

wherein substituents X and Ar are as set forth below:

d) X=Phe, Ar=3ClPh;
f) X=Phe, Ar=4ClPh;
h) X=Phe, Ar=2,5diClPh;
j) X=Phe, Ar=6FBnThz;
k) X=Phe, Ar=6ClBnThz;
l) X=pCl-Phe, Ar=6ClBnThz.

17. A composition of matter, denominated herein as 9(d), according to claim 16 wherein X=Phe and Ar=3ClPh.

18. A composition of matter, denominated herein as 9(f), according to claim 16 wherein X=Phe and Ar=4ClPh.

19. A composition of matter, denominated herein as 9(h), according to claim 16 wherein X=Phe and Ar=2,5diClPh.

20. A composition of matter, denominated herein as 9(j), according to claim 16 wherein X=Phe and Ar=6FBnThz.

21. A composition of matter, denominated herein as 9(k), according to claim 16 wherein X=Phe and Ar=6ClBnThz.

22. A composition of matter, denominated herein as 9(l), according to claim 16 wherein X=pCl-Phe and Ar=6ClBnThz.

23. A method of synthesizing the compositions of claim 16 which comprises:

(a) reacting an amine selected from the group consisting of: 4-fluoroaniline (2a); 2-chloroaniline (2b); 3-chloroaniline (2c); 4-chloroaniline C2d); 2,5-dichloroaniline (2e); 4-chlorophenethylamine (2f); 2-amino-6-fluorobenzothiazole (2g); 2-amino-6-chlorobenzothiazole (2h); 2-aminobenzothiazole (2i); 2-aminopyridine (2j); and 3-aminoquinoline (2k) with a Boc-L-amino acid selected from the group consisting of: N-tert-Boc-Phenylalanine (1b); and N-tert-Boc-p-chloro-Phenylalanine (1f) in the presence of a condensing agent selected from the group consisting of: 2-ethoxy-1-ethoxycarbonyl-1,2-dihydroquinoline (EEDQ); isobutylchloroformate; and 1,3-dicyclohexylcarbodiimide to form an amide;

(b) removing the protecting group from said amide with a reagent selected from the group consisting of: hydrogen chloride in acetic acid; hydrogen chloride in dioxane; and trifluoroacetic acid in methylene chloride, to afford the corresponding hydrochloride/trifluoroacetate salt;

(c) coupling said detected N-tert-butyloxycarbonyl-L-amino acid amide with dolaproine in the presence of diethylphosphorocyanidate and triethylamine to form a protected dipeptide amide;

(d) removing the protecting group of the protected dipeptide amide with trifluoroacetic acid to form a corresponding trifluoroacetate salt; and (e) coupling each of said trifluoroacetate salts with tripeptide trifluoroacetate (TFA* Dov-Val-Dil-OH) in the presence of diethylphosphorocyanidate to form said synthetic composition.

* * * * *